(12) United States Patent
Friedman

(10) Patent No.: US 10,898,463 B2
(45) Date of Patent: Jan. 26, 2021

(54) HIGH-STRENGTH ORAL CANNABINOID DOSAGE FORMS

(71) Applicant: ICDPHARMA LTD, Carme-Yosef (IL)

(72) Inventor: Doron Friedman, Carme-Yosef (IL)

(73) Assignee: ICDPHARMA LTD, Carme-Yosef (IL)

( * ) Notice: Subject to any disclaimer, the term of this patent is extended or adjusted under 35 U.S.C. 154(b) by 0 days.

(21) Appl. No.: 16/317,064

(22) PCT Filed: Jul. 12, 2017

(86) PCT No.: PCT/IL2017/050793
§ 371 (c)(1),
(2) Date: Jan. 11, 2019

(87) PCT Pub. No.: WO2018/011808
PCT Pub. Date: Jan. 18, 2018

(65) Prior Publication Data
US 2019/0298683 A1    Oct. 3, 2019

(30) Foreign Application Priority Data

Jul. 14, 2016 (IL) .......................................... 246790

(51) Int. Cl.
| | | |
|---|---|---|
| *A61K 36/00* | (2006.01) |
| *A61K 31/352* | (2006.01) |
| *A61P 25/18* | (2006.01) |
| *A61K 9/107* | (2006.01) |
| *A61K 31/01* | (2006.01) |
| *A61K 31/045* | (2006.01) |
| *A61K 36/185* | (2006.01) |
| *A61P 25/00* | (2006.01) |
| *A61K 31/05* | (2006.01) |

(52) U.S. Cl.
CPC .......... *A61K 31/352* (2013.01); *A61K 9/1075* (2013.01); *A61K 31/01* (2013.01); *A61K 31/045* (2013.01); *A61K 31/05* (2013.01); *A61K 36/185* (2013.01); *A61P 25/00* (2018.01); *A61P 25/18* (2018.01)

(58) Field of Classification Search
CPC ..................................................... A61K 36/00
USPC ......................................................... 424/725
See application file for complete search history.

(56) References Cited

U.S. PATENT DOCUMENTS

| | | |
|---|---|---|
| 2007/0104741 A1 | 5/2007 | Murty et al. |
| 2007/0270449 A1 | 11/2007 | Barlow et al. |

FOREIGN PATENT DOCUMENTS

| | | |
|---|---|---|
| WO | 2012/033478 A1 | 3/2012 |
| WO | 2015/048508 A1 | 4/2015 |
| WO | 2015068052 A2 | 5/2015 |
| WO | 2017149392 A1 | 9/2017 |

OTHER PUBLICATIONS

Supplementary European Search Report for EP 17 82 7129 dated Feb. 14, 2020.

*Primary Examiner* — Michael V Meller
(74) *Attorney, Agent, or Firm* — Browdy and Neimark, PLLC

(57) ABSTRACT

The present invention provides self-emulsifying, high concentration and high dose cannabinoid compositions and formulations, to improve administration of cannabinoids and standardized marijuana extracts to patients.

11 Claims, 9 Drawing Sheets

HIGH-STRENGTH ORAL CANNABINOID DOSAGE FORMS

FIELD OF THE INVENTION

The present invention relates to self-emulsifying, high concentration and high dose cannabinoid compositions and formulations, to improve administration of cannabinoids and standardized marijuana extracts to patients.

BACKGROUND OF THE INVENTION

*Cannabis* is one of the most widely used herb for medication. The medical use of *cannabis* is now legal in many countries under specific "medical *cannabis*" legislation. Medical *cannabis* is used for treating and alleviating symptoms associated with a growing number of indications, including pain, anorexia, asthma, glaucoma, arthritis, spasms, anxiety, and substance withdrawal. Many other illnesses are emerging as potential *cannabis*-responsive indications.

Borderline personality disorder (BPD) is a prevalent, chronic and debilitating psychiatric disorder. It affects approximately 1-2% of the general population, up to 10% of psychiatric outpatients, and 20% of inpatients. BPD is characterized by a pervasive pattern of instability in affect regulation, impulse control, interpersonal relationships, and self-image, beginning in adolescence and continues into adulthood. The prominent clinical presentation of the disorder includes depressive and anxiety symptoms, emotional dysregulation, impulsive aggression, repeated self-injury, and chronic suicidal behaviors, which make these patients frequent and heavy users of mental-health resources. BPD is conceived to be one of the most complicated mental illnesses, in need of a stabilizing pharmacological treatment. To-date, there is no FDA-approved pharmacological therapy for BPD. Several psychiatric medications are used to decrease the symptoms of the patients, but the effect is often mild, partial, temporary and generally unsatisfactory.

The most prevalent mode of use of *cannabis* is by smoking. Smoking is a less desirable mode of administration for drugs, including medical *cannabis*, since it has adverse effects on the lungs. *Cannabis* smoke carries more tar and other particulate matter than tobacco, and may be a cause of lung diseases including lung cancer. Furthermore, many patients find the act of smoking unappealing. More, since inhaled *cannabis* is short acting in pain reduction, it has to be smoked several times a day. Smoke *cannabis* in public is further unappealing to most people due to social constraints.

Another common mode of administration of medical *cannabis* is by dissolving the *cannabis* extract or pure cannabinoid in triglyceride oils, such as vegetable oils, for oral delivery. The oil is either filled into capsules or used as-is in various volumes. In contrast to inhalation, the oral route of drug administration is most convenient to most people, and is perceived as an acceptable mode of self-medication, such as consuming a pill. In such cases, an immediate release of the cannabinoids is obtained with fast absorption and an intermediate duration time of activity, but longer than smoking or vaporizing. A major drawback of dissolving cannabinoids in triglyceride oils is the inability to reach high concentrations of cannabinoids in a single unit dose, due to the limited solubility of cannabinoids and specifically cannabidiol in vegetable oils. Therefore, many products are "*cannabis* oils" which are cannabinoids dissolved in a vegetable oil and administered in relatively large volumes. However, a limitation of this approach is the unfavorable taste and smell, characteristic of the vegetable oils and cannabinoids, which often result in poor patient compliance.

High oral dose of cannabinoids and specifically cannabidiol (CBD) are required for treating many diseases. Cannabidiol for treating various psychiatric indications is prescribed at doses of 100 to 600 mg/day. Jalali and Johnson (International Neuropsychiatric Disease Journal, 2013, Vol. 1(2), pages 113-147) review numerous studies using THC and/or CBD for antipsychotic activity using 140 to 600 mg/day. Yeshurun and co-workers (Biol. Blood Marrow Transplant, 2015, Vol. 21(10), pages 1770-1775) successfully treated Graft-versus-host-disease (GVHD) using pure CBD at a dose of 600 mg/day. Devinsky and co-workers (Epilepsia, 2014, Vol. 55(6), pages 791-802) used 200 to 300 mg of CBD for treating anticonvulsant in epilepsy and other neurological disorders. Leweke and co-workers (Psychiatry, 2012, Vol. 15, pages 2012-2015) used up to 800 mg cannabidiol per day to alleviate psychotic symptoms of schizophrenia. Hurd and co-workers, (Neurotherapeutics, 2015, pages 607-15) used 400 and 800 mg cannabidiol as treatment for opioid addiction. Devinsky and co-workers, (The lancet neurology, 2016, Vol. 15(3) pages 270-278) treated patients with treatment-resistant epilepsy with median 23 mg/kg cannabidiol which is 500 mg to >1,000 mg per day for many patients. Chagas and co-workers (Journal of psychopharmacology, 2014, Vol 28(11), pages 1088-1092) treated Parkinson's disease with 300 mg of cannabidiol.

Therefore, there is a need for high dosage of cannabinoids, e.g. over 100 mg and over 300 mg per unit dose, and a patient-friendly oral delivery system, that will improve patient compliance by reducing number of daily administration to e.g. once or twice daily. This proves problematic as cannabinoids are lipophilic molecules which are not soluble in water and have low and variable oral bioavailability. For example, Marinol® is marketed with THC as the active ingredient, dissolved in sesame oil. Oral THC bioavailability was reported to be only 10-20% (Wall et al., Clinical Pharmacology & Therapeutics, 1983, Vol. 34(3), pages 352-363).

Due to their poor solubility in physiological fluids, it is also an unmet need to have a high dose of cannabinoid in a single oral dosage form, that solubilize the cannabinoids upon mixture with the body physiological gastro-intestinal fluids to facilitate bio-absorption. To overcome low oral bioavailability, various lipid-based drug delivery systems and self-emulsifying systems were developed. Lipid-based delivery systems and particularly self-emulsifying drug delivery systems (SEDDS) were demonstrated to increase the solubility, dissolution and bioavailability of many insoluble drugs. However, lipid-based and SEDDS delivery systems are also very limited by the amount of drug loading that has to be dissolved in the vehicle composition, usually ranging from 1% to 10%. Higher concentration of active pharmaceutical ingredients (APIs) are obtained using co-solvents, which enable drug loads of up to 30% in specific cases.

U.S. Pat. Nos. 6,730,330 and 7,025,992 relate to pharmaceutical formulations for use in the administration of medicaments, in particular lipophilic medicaments, via mucosal surfaces, and describe composition containing 3%-20% by weight cannabinoids. U.S. Patent Application Publication no. 2007/104741 relates to a self-emulsifying drug delivery system of dronabinol or other cannabinoids. U.S. Pat. No. 9,265,724 relates to self-emulsifying drug delivery systems including dronabinol or other cannabinoids, an oily medium and a surfactant. International Patent Application Publication no. WO 2015/068052 relates to liposomal and micellar formulations of one or more terpenes, optionally in combination with one or more cannabinoids.

There remains an unmet need for high-cannabinoid-concentration compositions and high-dose cannabinoid dosage forms, e.g. for the treatment of various clinical targets. Such products will enable administering therapeutically-effective amounts of cannabinoids in a single unit dose, and provide patients with a convenient route of cannabinoid administration to improve patient compliance. It would also be preferable that such products produce fine particles of cannabinoids in the gastro-intestinal fluids to facilitate gastric absorption.

SUMMARY OF THE INVENTION

The present invention relates to compositions, formulations and delivery systems, for the administration of high loads of cannabinoids to patients, and improving patient compliance. More particularly, the present invention relates to compositions and dosage forms of cannabinoids, terpenes and emulsifiers, which quickly self-emulsify and produce micron and sub-micron particles, thereby enhancing bioavailability through the gastrointestinal tract.

The inventor has unexpectedly discovered that it is possible to have self-emulsifying delivery system of high loads of *cannabis* extracts and pure cannabinoids, without the use of oils and/or co-solvents, while reaching unprecedented concentrations of cannabinoids. Such findings led to the discovery of the pharmaceutical compositions and formulations of the present invention, which are demonstrated herein to possess several therapeutically-beneficial properties. For example, the pharmaceutical, medicinal, veterinary or cosmetic compositions of the present invention comprise high loads and concentrations of cannabinoids, reaching up to about 90% by weight of the pharmaceutical compositions. Secondly, the compositions of the present invention self-emulsify very quickly upon hydration with water or intestinal fluids, usually within several minutes, thus instantly releasing their entire load of cannabinoids into emulsion form. More, the pharmaceutical compositions of the present invention self-emulsify upon hydration to produce very fine micron and submicron droplets, thus enabling their entire load of cannabinoids to be biologically available.

The present invention provides, in one aspect, a self-emulsifying composition, comprising: about 20% to about 90% by weight of a cannabinoid or a mixture of cannabinoids, about 5% to about 50% by weight of a terpene or a mixture of terpenes, and about 5% to about 50% by weight of an emulsifier or a mixture of emulsifiers, wherein the composition self-emulsifies in an aqueous medium to produce a plurality of particles having a mean particle size of about 100 microns to about 10 nm.

In certain embodiments, the composition is a pharmaceutical composition. In certain embodiments, the composition is a cosmetic composition. In certain embodiments, the composition is a veterinary composition.

The term "pharmaceutical composition" as used herein has its conventional meaning and refers to a composition which is pharmaceutically acceptable. The term "pharmaceutically acceptable" as used herein has its conventional meaning and refers to compounds, material, compositions and/or dosage forms, which are, within the scope of sound medical judgment suitable for contact with the tissues of mammals, especially humans, without excessive toxicity, irritation, allergic response and other problem complications commensurate with a reasonable benefit/risk ratio. The term "excipient" as used herein has its conventional meaning and refers to a pharmaceutically acceptable ingredient, which is commonly used in the pharmaceutical technology for preparing a granulate, solid or liquid oral dosage formulation. The term "cosmetic composition" is intended to mean a substance or a preparation intended to be brought into contact with the various superficial parts of the body, in particular the epidermis, the body-hair and head-hair systems, the nails, the lips and the oral mucous membranes. The term "veterinary composition" encompasses the full range of compositions for internal administration and feeds and drinks which can be consumed by animals. Typical veterinary dosage forms for internal administration are orally administrable dosage forms, such as pastes, solutions, tablets, etc. However, injectable compositions are also envisaged. The compositions of the present invention may also be medicated fodders, feeds, nutriments, premixes, drinking waters and drinking water additives. Typically, for mixing in feed, the composition is provided as a powder and for mixing in drinking water the composition is provided as a fluid.

In certain embodiments, the pharmaceutical composition further comprises about 10% to about 25% by weight of a viscosity-modifying agent or a mixture of viscosity-modifying agents.

In certain embodiments, the pharmaceutical composition comprises about 30% to about 80% by weight of a cannabinoid or a mixture of cannabinoids. In certain embodiments, the composition comprises about 40% to about 70% by weight of a cannabinoid or a mixture of cannabinoids. In certain embodiments, the cannabinoid is selected from the group consisting of cannabidiol (CBD), cannabidiolic acid (CBDA), tetrahydrocannabinol (THC), tetrahydrocannabinolic acid (THCA), cannabigerol (CBG), cannabichromene (CBC), cannabinol (CBN), cannabielsoin (CBE), iso-tetrahydrocannabimol (iso-THC), cannabicyclol (CBL), cannabicitran (CBT), cannabivarin (CBV), tetrahydrocannabivarin (THCV), cannabidivarin (CBDV), cannabichromevarin (CBCV), cannabigerovarin (CBGV), cannabigerol monomethyl ether (CBGM), salts thereof, derivatives thereof and mixtures of cannabinoids.

In certain embodiments, the pharmaceutical composition comprises about 5% to about 35% by weight of a terpene or a mixture of terpenes. In certain embodiments, the pharmaceutical composition comprises about 5% to about 20% by weight of a terpene or a mixture of terpenes. In certain embodiments, the terpene is selected from the group consisting of bisabolol, borneol, caryophyllene, carene, camphene, cineol, citronella, eucalyptol, geraniol, guaiol, humulene, isopropyltoluene, isopulegol, linalool, limonene, menthol, myrcene, nerolidol, ocimene, pinene, phytol, pulegone, terpinene, terpinolene, thymol, salts thereof, derivatives thereof, and mixtures of terpenes.

In certain embodiments, the weight ratio between the a cannabinoid and the a terpene is about 20:1 to about 0.5:1. In certain embodiments, the weight ratio between the a cannabinoid and the a terpene is about 25:1 to about 1:1. In certain embodiments, the weight ratio between the a cannabinoid and the a terpene is about 20:1 to about 1:1. In certain embodiments, the weight ratio between the cannabinoid and the terpene is about 15:1 to about 1:1. In certain embodiments, the weight ratio between the cannabinoid and the emulsifier is about 0.5:1 to about 10:1. In certain embodiments, the natural cannabinoid or the natural terpene is derived from an extract of a *Cannabis* plant. In certain embodiments, the terpene solubilizes a cannabinoid.

In certain embodiments, the pharmaceutical composition comprises about 5% to about 25% by weight of an emulsifier or a mixture of emulsifiers. In certain embodiments, the pharmaceutical composition comprises about 25% to about 50% by weight of an emulsifier or a mixture of emulsifiers. In certain embodiments, the emulsifier is selected from the group consisting of polysorbate 80, oleoyl polyoxyl-6 glycerides, polyoxyl 35 hydrogenated castor oil, sucrose distearate, tocopherol polyethylene glycol 1000 succinate, lauroyl polyoxyl-32 glycerides, sorbitan monooleate, salts thereof, derivatives thereof, and mixtures of emulsifiers.

In certain embodiments, the pharmaceutical composition self-emulsifies to produce a plurality of particles having a mean particle size of 10 microns or less. In certain embodiments, the pharmaceutical composition self-emulsifies to produce a plurality of particles having a mean particle size of 5 microns or less. In certain embodiments, the pharmaceutical composition self-emulsifies to produce a plurality of particles having a mean particle size of 2 microns or less. In certain embodiments, the pharmaceutical composition self-emulsifies in water at 37° C. within less than 1 hour under light agitation. In certain embodiments, at least 80% by weight of the pharmaceutical composition self-emulsifies within less than 30 minutes. In certain embodiments, at least 80% by weight of the pharmaceutical composition self-emulsifies within 2 minutes. In certain embodiments, at least 80% by weight of the pharmaceutical composition self-emulsifies within 30 seconds. In certain embodiments, the pharmaceutical composition self-emulsifies to produce a plurality of particles, wherein at least 80% of the particles have a size of 30 microns or less. In certain embodiments, the pharmaceutical composition self-emulsifies to produce a plurality of particles, wherein at least 90% of the particles have a size of 10 microns or less.

In certain embodiments, the pharmaceutical composition self-emulsifies in water at 37° C. within less than 1 hour under light agitation. In certain embodiments, at least 80% by weight of the pharmaceutical composition self-emulsifies within less than 30 minutes. In certain embodiments, at least 80% by weight of the pharmaceutical composition self-emulsifies within 2 minutes. In certain embodiments, at least 80% by weight of the pharmaceutical composition self-emulsifies within 30 seconds. In certain embodiments, the pharmaceutical composition self-emulsifies to produce a plurality of particles, wherein at least 80% of the particles have a size of 30 microns or less. In certain embodiments, the pharmaceutical composition self-emulsifies to produce a plurality of particles, wherein at least 90% of the particles have a size of 10 microns or less. In certain embodiments, the pharmaceutical composition self-emulsifies to produce a plurality of particles having a mean particle size of 10 microns or less. In certain embodiments, the pharmaceutical composition self-emulsifies to produce a plurality of particles having a mean particle size of 5 microns or less. In certain embodiments, the pharmaceutical composition self-emulsifies to produce a plurality of particles having a mean particle size of 1 microns or less.

In certain embodiments, the pharmaceutical composition is formulated for slow release of a cannabinoid or a mixture of cannabinoids upon self-emulsification. In certain embodiments, the pharmaceutical composition further comprises a release retarding agent or a mixture of release retarding agents. In certain embodiments, the pharmaceutical composition comprises about 1% to about 20% by weight of a release retarding agent or a mixture of release retarding agents. In certain embodiments, the pharmaceutical composition comprises about 5% to about 15% by weight of a release retarding agent or a mixture of release retarding agents.

In certain embodiments, the release retarding agent is a high-molecular-weight polymer or a mixture of high-molecular-weight polymers. In certain embodiments, the high-molecular-weight polymer is selected from the group consisting of cellulose derivatives such as ethyl cellulose or hydroxypeopyl methyl cellulose (HPMC), hydroxyl ethyl cellulose, cellulose phthalate, polyvinylpyrrolidone (PVP), polyvinyl alcohol (PVA), polyvinyl caprolactam, polyvinyl acetate, polyethylene glycol graft copolymer, acrylates and acrilyc polymers, methyl acrylate, methacrylic acid/ethyl acrylate copolymers, alkyl acrylate or cross linked acrylates, natural polysacchariseds, such as xanthan gum, guar gum, locust bean gum, gum arabica, pectin, zein, karaya gum, alginate, hyaluronic acid, chitosan, starch, ppolyethylene glycols or polyethylene glycols and polypropylene glycols block copolymers, and mixtures thereof.

In certain embodiments, the high-molecular-weight polymer is selected from the group consisting of ethyl cellulose, hydroxypropyl methyl cellulose, polyvinylpyrrolidone, alkyl acrylate, acrilyc polymer, xanthan gum, guar gum, zein and mixtures of high-molecular-weight polymers.

In certain embodiments, the pharmaceutical composition self-emulsifies to produce a plurality of particles having a mean particle size of 10 microns or less upon hydration. In certain embodiments, the pharmaceutical composition self-emulsifies to produce a plurality of particles having a mean particle size of 2 microns or less.

In certain embodiments, the pharmaceutical composition is formulated for delayed release of a cannabinoid or a mixture of cannabinoids. In certain embodiments, the pharmaceutical composition is at least partly coated by an enteric-coating agent.

In certain embodiments, the pharmaceutical composition is liquid at room temperature. In certain embodiments, the pharmaceutical composition is semi-solid at room temperature. In certain embodiments, the pharmaceutical composition is solid at room temperature.

The present invention further provides, in another aspect, a dosage form, comprising any one of the compositions described above, or a mixture of the pharmaceutical compositions described above.

In certain embodiments, the dosage form comprises at least about 50 mg of a cannabinoid or a mixture of cannabinoids. In certain embodiments, the dosage form comprises about 50 mg to about 1,200 mg of a cannabinoid or a mixture of cannabinoids. In certain embodiments, the dosage form comprises about 100 mg, about 200 mg, about 300 mg, about 400 mg, about 500 mg or about 600 mg of a cannabinoid or a mixture of cannabinoids.

In certain embodiments, the dosage form comprises is formulated as a hard shell capsule, a soft shell capsule, a tablet, a liquid, a syrup or enema. In certain embodiments, the dosage form comprises is formulated for oral or mucosal delivery. In certain embodiments, the dosage form is formulated as or in a lozenge, candy, toffee, chocolate or cookie.

In certain embodiments, any one of the compositions described above, or any one of the dosage forms described above, is for use in a method of treating a cannabinoid-responsive symptom, disease or disorder.

In certain embodiments, any one of the compositions described above, or any one of the dosage forms described above, is for use in a method of treating borderline personality disorder (BPD) or a BPD-related symptom or reducing the number or dose of drugs used for treating BPD.

In certain embodiments, treating comprises improvement in scores of one or more of the rating scales selected from the group consisting of Borderline Symptom List 23 (BSL-23); Borderline Symptom List 95 (BSL-95); Brief Psychiatric Rating Scale (BPRS); Hamilton Anxiety (HAM-A); Hamilton Depression (HAM-D); Barratt Impulsiveness Scale (BIS-11); Pittsburgh Sleep Quality Index (PSQI); Columbia-Suicide Severity Rating Scales (C-SSRS); Columbia Non-Suicidal Self-Injury Rating Scale; Sheehan Disability Scale (SDS); Fagerstrom test for nicotine dependence (FTND); Pain Catastrophizing symptoms questionnaire (PCS); and Zanarini Rating Scale for BPD (ZAN-BPD).

In certain embodiments, the composition or dosage form comprises cannabidiol (CBD). In certain embodiments, the pharmaceutical composition or dosage form further comprises tetrahydrocannabinoid (THC). In certain embodiments, the CBD:THC weight ratio is about 20:1. In certain embodiments, the mixture of a cannabinoid and a terpene is a cannabinoid extract. In certain embodiments, the mixture of a cannabinoid and a terpene is a *cannabis* extract. In certain embodiments, the mixture comprises CBD. In certain embodiments, the mixture comprises THC. In certain embodiments, the mixture comprises CBD and THC. In certain embodiments, the mixture comprises CBD and THC in a weight ratio of about 1:1.

The present invention further provides, in another aspect, a method of treating borderline personality disorder (BPD) in a subject in need thereof, comprising administering a composition comprising therapeutically-effective amount of cannabidiol (CBD) to the subject.

In certain embodiments, the pharmaceutical composition further comprises one or more cannabinoids other than CBD, wherein the pharmaceutical composition comprises about 20% to about 90% by weight of cannabinoids. In certain embodiments, the pharmaceutical composition comprises about 20% to about 90% by weight of the CBD. In certain embodiments, the pharmaceutical composition further comprises about 5% to about 50% by weight of a terpene or a mixture of terpenes. In certain embodiments, the pharmaceutical composition further comprises about 5% to about 50% by weight of an emulsifier or a mixture of emulsifiers. In certain embodiments, the pharmaceutical composition further comprises about 10% to about 25% by weight of a viscosity-modifying agent or a mixture of viscosity-modifying agents. In certain embodiments, the pharmaceutical composition self-emulsifies in an aqueous medium to produce a plurality of particles having a mean particle size of less than 100 microns or a mean particle size of about 100 microns to about 10 nm.

In certain embodiments, the pharmaceutical composition self-emulsifies to produce a plurality of particles having a mean particle size of 10 microns or less upon hydration. In certain embodiments, the pharmaceutical composition self-emulsifies to produce a plurality of particles having a mean particle size of 1 microns or less.

In certain embodiments, the pharmaceutical composition further comprises about 0% to about 70% by weight of triglycerides, fats, lipids, oils other than essential oils, fatty acids, co-solvents or mixtures thereof.

The present invention further provides, in an aspect, a method for producing a composition as described above or a dosage form as described above, comprising the steps of melting and mixing the cannabinoid, the terpene, the emulsifier and optionally the release retarding agent, and further optionally comprising the steps of cooling the mixture; filling a soft or hard shell capsule with the mixture; or forming granules that are optionally entero-coated and used as is or further compressed into tablet or filled into capsule and at least partly coating the mixture, the granules, or the capsule or tablet; and any combination thereof. Another optional method for producing a composition as described above or a dosage form as described above comprises the step of melting all ingredients besides the cannabinoid(s), and further optionally comprises the step of cooling the mixture for future use. Later, the use comprises the step of heating and melting the mixture and further adding and mixing the cannabinoid(s) and cooling the mixture and forming a desired dosage form.

The methods, uses, materials, and examples that will now be described are illustrative only and are not intended to be limiting; materials, uses and methods similar or equivalent to those described herein can be used in practice or testing of the invention. Other features and advantages of the invention will be apparent from the following figures, detailed description, and from the claims.

DETAILED DESCRIPTION OF THE INVENTION

Figure 1:
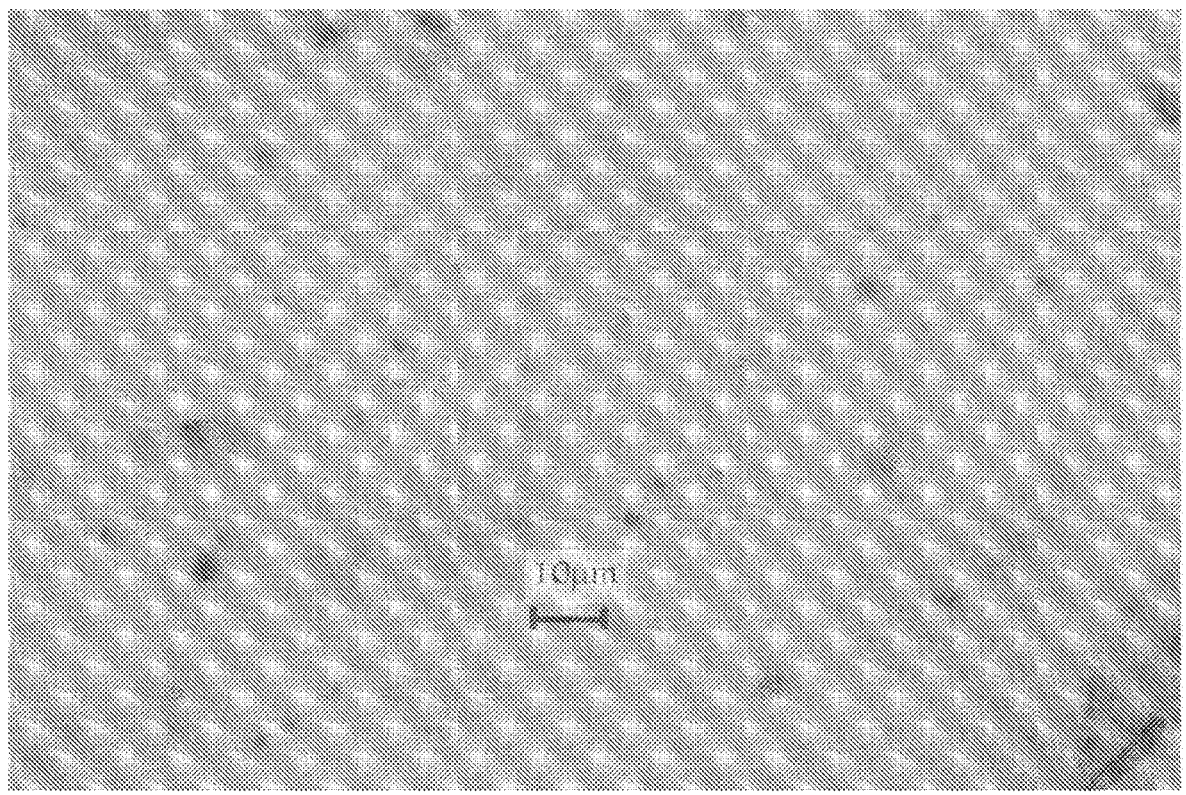
FIG. 1 is a light microscope picture of fine particles of formulation F002 formed within seconds after dilution 1:10 in water (magnification ×200).

Provided by the present invention are self-emulsifying compositions and dosage forms having high loads of cannabinoids and cannabinoid mixtures. Due to their high cannabinoid content, these dosage forms can replace others, having lower cannabinoid content, which minimizes the need for repetitive administration while treating *cannabis*-responsive diseases, syndromes and symptoms. Besides their superior cannabinoid content, the pharmaceutical compositions and dosage forms provided by the present invention readily and quickly self-emulsify in biological fluids under physiological conditions to produce fine particles which are highly bioavailable. The small droplet size, formed upon emulsification, is associated with improved stability. Moreover, the high droplet surface area associated with the small droplet size often leads to a high reactivity with biological cells and macromolecules (Annu. Rev. Food Sci. Technol., 2017, Vol. 8, pages 439-466).

Without being limited to any theory or mechanism, the present invention is based on the surprising finding that terpenes, either synthetic or found naturally in *Cannabis* plants and other plants, are exceptionally proficient, optionally in combination with emulsifiers, in dissolving large amounts of cannabinoids, and thus producing self-emulsifying formulations with high concentrations of cannabinoids.

The present invention provides, in one aspect, a self-emulsifying composition, comprising: about 20% to about 90% by weight of a cannabinoid or a mixture of cannabinoids, about 5% to about 50% by weight of a terpene or a mixture of terpenes, and about 5% to about 50% by weight of an emulsifier or a mixture of emulsifiers, wherein the composition self-emulsifies in an aqueous medium to produce a plurality of particles having a mean particle size of about 100 microns to about 10 nm.

The term "cannabinoid" as used herein generally refers to one of a class of diverse chemical compounds that act on a cannabinoid receptor in cells that repress neurotransmitter release in the brain. The term "cannabinoid" as used herein further refers a chemical compounds that acts on cannabinoid receptors or has a structure similar the stature of a compound acting on cannabinoid receptor in cells. Ligands for these receptor proteins include the endocannabinoids (produced naturally in the body by humans and animals), the phytocannabinoids (found in *cannabis* and some other plants), and synthetic cannabinoids (manufactured artificially).

The present invention provides, in another aspect, a self-emulsifying composition, comprising (i) about 60% to about 90% by weight of a *cannabis* extract, comprising (a) a cannabinoid or a mixture of cannabinoids and (b) a terpene or a mixture of terpenes; and (ii) about 5% to about 40% by weight of an emulsifier or a mixture of emulsifiers, wherein the composition self-emulsifies in an aqueous medium to produce a plurality of particles having a mean particle size of about 100 microns to about 10 nm.

The term "*cannabis* extract" as used herein refers to one or more plant extracts from the *cannabis* plant. A *cannabis* extract contains, in addition to one or more cannabinoids, one or more non-cannabinoid components which are co-extracted with the cannabinoids from the plant material. Their respective ranges in weight will vary according to the starting plant material and the extraction methodology used. Cannabinoid-containing plant extracts may be obtained by various means of extraction of *cannabis* plant material. Such means include but are not limited to: supercritical or sub-critical extraction with $CO_2$, extraction with hot or cold gas and extraction with solvents.

The term "terpene" as used herein also covers terpenoids. Terpenes are lipophilic compounds, volatile and liquid at room temperature and are used herein in this invention as cannabinoids solubilizing agents. Terpenes are major secondary metabolites of *cannabis* and are responsible for the odor and flavor of various *cannabis* strains. *Cannabis* strains and hemp strains produce many terpenes as secondary metabolites. Terpenes are synthetized from terpene unit into mono-terpenes, sesqui-terpenes, di-terpenes that are lipophilic, volatile and insoluble in water and are cyclic or bicyclic or not cyclic and may have alcohol, aldehyde or ketone chemical moiety. The term "terpene" further relates to essential oils. The term "terpene" does not include fats and/or lipids.

In certain embodiments, the pharmaceutical composition is substantially devoid of fats and/or oils except essential oils. The term "essential oils" as used herein refers to a concentrated hydrophobic liquid containing volatile aroma compounds from a plant. Essential oils are also known as volatile oils, ethereal oils, aetherolea, or the oil of the plant from which they were extracted. As used herein, the term "fat" refers to saturated, mono-unsaturated and poly-unsaturated fatty acid. Fatty acids are usually present in the form of esters (e.g. mono-/di-/triglycerides). As used herein the term "oil" is used as a generic term for lipids, fats, or any mixture thereof.

Generally, terpenes are derived biosynthetically from units of isoprene, which has the molecular formula $C_5H_8$. The basic molecular formulas of terpenes are multiples of $(C_5H_8)_n$ where n is the number of linked isoprene units. As chains of isoprene units are added, the resulting terpenes are classified sequentially by size as hemiterpenes, monoterpenes, sesquiterpenes, diterpenes, sesterterpenes, triterpenes, and tetraterpenes. Essentially, they are all synthesized by terpene synthase.

The term "about" as used herein refers to any value which lies within a range of ±5% of original value. For example, "about 100" refers to "95 to 105".

The term "emulsifier" as used herein are amphiphilic molecules that are surface active agents and that stabilize emulsions by reducing the interfacial tension.

The term "self-emulsifying composition" as used herein refers to a composition that forms an emulsion when placed in an aqueous medium. According to the principles of the present invention, a self-emulsifying composition is not by itself an emulsion, i.e. it does not comprise a mixture of two or more liquids that are normally immiscible (unmixable or unblendable).

In certain embodiments, the pharmaceutical composition of the present invention is a non-aqueous composition. The term "non-aqueous" as used herein refer to compositions devoid or substantially devoid of water. In certain embodiments, the pharmaceutical composition of the present invention is non-liposomal composition. In certain embodiments, the pharmaceutical composition of the present invention is non-micellar composition. In certain embodiments, the pharmaceutical composition of the present invention is non-liposomal and non-micellar composition. In certain embodiments, the particle or particles of the present invention are non-liposomal particle or particles. In certain embodiments, the particle or particles of the present invention are non-micellar particle or particles. In certain embodiments, the particle or particles of the present invention are non-liposomal and non-micellar particle or particles. Each possibility represents a separate embodiment of the invention. The terms "non-liposomal" and "non-micellar" as used herein refer to compositions and particles devoid or substantially devoid of liposomes and/or micelles.

In certain embodiments, the self-emulsifying composition forms an emulsion when placed in an aqueous medium, wherein the emulsion is stable for at least 24 hours. In certain embodiments, the aqueous medium is water. In certain embodiments, the aqueous medium is an intestinal fluid. In certain embodiments, the aqueous medium is a gastrointestinal fluid, or simulated intestinal or gastric fluids.

As used herein, the term "particles" as used herein relates to droplets. The term "particle size" of an emulsion is to be understood also as the "droplet size" of that emulsion. The term "mean particle size" is also to be understood as the term "mean droplet size".

As used herein, the term "mean particle size" refers to a value which is obtained by measuring the diameters in a specific direction of particles and dividing the sum of respective diameters of particles by the number of measured particles.

In certain embodiments, the pharmaceutical composition further comprises about 10% to about 25% by weight of a viscosity-modifying agent or a mixture of viscosity-modifying agents.

The term "viscosity modifier" or "a viscosity-modifying agent" as used herein refers to any additive that can modify the pharmaceutical composition viscosity to a desired viscosity level (either higher or lower). Typical example include, without limitation solvents, lubricants and gelling agents. The viscosity modifier component can comprise one or more viscosity modifier. As used herein, the term "viscosity modifier" is further intended to mean a compound or mixture of compounds that can be used to adjust the viscosity of a composition of the invention. Suitable viscosity modifiers include microcrystalline wax, glyceryl dibehenate, hydrogenated castor oil wax MP80, and others recognized by artisans in the field. In certain embodiments, the viscosity modifier is selected from the group consisting of microcrystalline wax, glyceryl dibehenate, hydrogenated castor oil wax MP80, and any combination thereof. Each possibility represents a separate embodiment of the invention.

In certain embodiments, the pharmaceutical composition comprises about 25% to about 85% by weight of a cannabinoid or a mixture of cannabinoids. In certain embodiments, the pharmaceutical composition comprises about 30% to about 80% by weight of a cannabinoid or a mixture of cannabinoids. In certain embodiments, the pharmaceutical composition comprises about 35% to about 75% by weight of a cannabinoid or a mixture of cannabinoids. In certain embodiments, the pharmaceutical composition comprises about 40% to about 70% by weight of a cannabinoid or a mixture of cannabinoids.

In certain embodiments, the pharmaceutical composition comprises at least about 25% to about 90% by weight of a cannabinoid or a mixture of cannabinoids. In certain embodiments, the composition comprises at least about 30% to about 90% by weight of a cannabinoid or a mixture of cannabinoids. In certain embodiments, the pharmaceutical composition comprises at least about 35% to about 90% by weight of a cannabinoid or a mixture of cannabinoids. In certain embodiments, the pharmaceutical composition comprises at least about 40% to about 90% by weight of a cannabinoid or a mixture of cannabinoids. In certain embodiments, the pharmaceutical composition comprises at least about 50% to about 90% by weight of a cannabinoid or a mixture of cannabinoids. In certain embodiments, the pharmaceutical composition comprises at least about 60% to about 90% by weight of a cannabinoid or a mixture of cannabinoids.

In certain embodiments, the cannabinoid is a natural cannabinoid. In certain embodiments, the cannabinoid is a natural cannabinoid found in a *Cannabis* plant. In certain embodiments, the cannabinoid is a synthetic cannabinoid. In certain embodiments, the cannabinoid is a mixture of natural cannabinoids. In certain embodiments, the cannabinoid is a mixture of synthetic cannabinoids. In certain embodiments, the cannabinoid is a mixture of natural and synthetic cannabinoids.

The term "natural cannabinoid" as used herein generally refers to a cannabinoid which can be found in, isolated from and/or extracted from a natural resource, such as plants. "Synthetic cannabinoids" are a class of chemicals that are different from the cannabinoids found e.g. in *cannabis* but which also bind to cannabinoid receptors.

In certain embodiments, the cannabinoid is selected from the group consisting of cannabidiol (CBD), cannabidiolic acid (CBDA), tetrahydrocannabinol (THC), tetrahydrocannabinolic acid (THCA), cannabigerol (CBG), cannabichromene (CBC), cannabinol (CBN), cannabielsoin (CBE), iso-tetrahydrocannabimol (iso-THC), cannabicyclol (CBL), cannabicitran (CBT), cannabivarin (CBV), tetrahydrocannabivarin (THCV), cannabidivarin (CBDV), cannabichromevarin (CBCV), cannabigerovarin (CBGV) and cannabigerol monomethyl ether (CBGM), salts thereof, derivatives thereof and mixtures of cannabinoids. Each possibility represents a separate embodiment of the invention.

The terms "cannabidiol" and "CBD" are interchangeably used herein and refer to a non-psychotropic cannabinoid having structure as described in Formula I below, salt or derivatives thereof, such as $\Delta^4$-cannabidiol, $\Delta^5$-cannabidiol, $\Delta^6$-cannabidiol, $\Delta^{1,7}$-cannabidiol, $\Delta^1$-cannabidiol, $\Delta^2$-cannabidiol, $\Delta^3$-cannabidiol.

Formula I

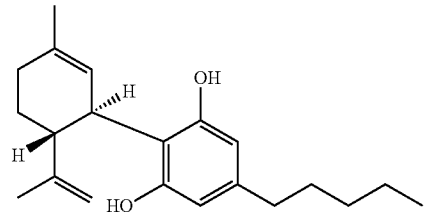

In another embodiment, the pharmacologically active cannabinoid may be selected from the group consisting of tetrahydrocannabinol, $\Delta$9-tetrahydrocannabinol (THC), $\Delta$8-tetrahydrocannabinol, standardized marijuana extracts, $\Delta$8-tetrahydrocannabinol-DMH, $\Delta$9-tetrahydrocannabinol propyl analogue (THCV), 11-hydroxy-tetrahydrocannabinol, 11-nor-9-carboxy-tetrahydrocannabinol, 5'-azido-.$\Delta$8-tetrahydrocannabinol, AMG-1 (CAS Number 205746-46-9), AMG-3 (CAS Number 205746-46-9), AM-411 (CAS Number 212835-02-4), (−)-11-hydroxy-7'-isothiocyanato-$\Delta$8-THC (AM-708), (−)-11-hydroxy-7'-azido-$\Delta$8-THC (AM-836), AM-855 (CAS Number 249888-50-4), AM-919 (CAS Number 164228-46-0), AM926, AM-938 (CAS Number 303113-08-8), cannabidiol (CBD), cannabidiol propyl analogue (CBDV), cannabinol (CBN), cannabichromene, cannabichromene propyl analogue, cannabigerol, CP 47,497 (CAS Number (1S,3R): 114753-51-4), CP 55,940 (CAS Number 83002-04-4), CP 55,244 (CAS Number 79678-32-3), CT-3 (ajulemic acid), dimethylheptyl HHC, HU-210 (1,1-Dimethylheptyl-11-hydroxy-tetrahydrocannabinol), HU-211 (CAS Number 112924-45-5), HU-308 (CAS Number 1220887-84-2), WIN 55212-2 (CAS Number 131543-22-1), desacetyl-L-nantradol, dexanabinol, JWH-051 (Formula $C_{25}H_{38}O_2$), levonantradol, L-759633 (Formula $C_{26}H_{40}O_2$), nabilone, O-1184, and mixtures thereof.

In another embodiment, the pharmacologically active cannabinoid may further be selected from the group consisting of palmitoylethanolamide (PEA), alkylethanolamide, oleyl-serine, cannabinomimetic, caryophyllene, CB1 and/or CB2 agonist and/or antagonist, partial agonist, reversible or not, and any combination thereof.

The cannabinoid may be included in its free form, or in the form of a salt; an acid addition salt of an ester; an amide; an enantiomer; an isomer; a tautomer; a prodrug; a derivative of an active agent of the present invention; different isomeric forms (for example, enantiomers and diastereoisomers), both in pure form and in admixture, including racemic mixtures; and enol forms.

In some embodiments, the cannabinoid(s) utilized in the present invention are a lipophilic concentrate of cannabinoid (s). In some embodiments, the cannabinoid(s) utilized in the present invention are a lipophilic concentrate of cannabinoid (s) achieved via $CO_2$, solvents or gas extraction techniques.

Extraction of *cannabis* plant of various plant parts, may be done by $CO_2$ extraction or by solvent extraction or solvent-less compression to obtain oily viscous material or waxy material or solid material, depends on plant material, plant parts and extraction methods as skilled in the art. Extraction and processing may result in broad spectrum of *cannabis* molecules, cannabinoids, terpenes and other families of natural *cannabis* molecules or in a pure extract of cannabinoids or concentrated cannabinoid terpenes extract. *Cannabis* or marijuana extract may be further decarboxylated, winterized and/or purified, for example by distillation, as known in the art.

In certain embodiments, the pharmaceutical composition comprises about 5% to about 45% by weight of a terpene or a mixture thereof. In certain embodiments, the pharmaceutical composition comprises about 5% to about 40% by weight of a terpene or a mixture thereof. In certain embodiments, the pharmaceutical composition comprises about 5% to about 35% by weight of a terpene or a mixture thereof. In certain embodiments, the pharmaceutical composition comprises about 5% to about 30% by weight of a terpene or a mixture thereof. In certain embodiments, the pharmaceutical composition comprises about 5% to about 25% by weight of a terpene or a mixture thereof. In certain embodiments, the pharmaceutical composition comprises about 5% to about 20% by weight of a terpene or a mixture thereof.

In certain embodiments, the pharmaceutical composition comprises about 30% to about 95% by weight of a mixture of the a cannabinoid and a terpene. In certain embodiments, the pharmaceutical composition comprises about 40% to about 95% by weight of a mixture of the a cannabinoid and a terpene. In certain embodiments, the pharmaceutical composition comprises about 50% to about 95% by weight of a mixture of the a cannabinoid and a terpene. In certain embodiments, the pharmaceutical composition comprises about 60% to about 95% by weight of a mixture of a cannabinoid and a terpene. In certain embodiments, the pharmaceutical composition comprises about 70% to about 95% by weight of a mixture of the a cannabinoid and a terpene. In certain embodiments, the pharmaceutical composition comprises about 80% to about 95% by weight of a mixture of the a cannabinoid and a terpene.

In certain embodiments of the pharmaceutical composition, the weight ratio between the cannabinoid and the terpene is about 25:1 to about 1:1. In certain embodiments of the pharmaceutical composition, the weight ratio between the cannabinoid and the terpene is about 20:1 to about 1:1. In certain embodiments of the pharmaceutical composition, the weight ratio between the cannabinoid and the terpene is about 15:1 to about 1:1. In certain embodiments of the pharmaceutical composition, the weight ratio between the cannabinoid and the terpene is about 10:1 to about 1:1. In certain embodiments of the pharmaceutical composition, the weight ratio between the cannabinoid and the terpene is about 5:1 to about 1:1.

In certain embodiments, the terpene is a natural terpene. In certain embodiments, the terpene is a natural terpene found in a *Cannabis* plant. In certain embodiments, the terpene is a synthetic terpene. In certain embodiments, the terpene is a mixture of natural terpenes. In certain embodiments, the terpene is a mixture of synthetic terpenes. In certain embodiments, the terpene is a mixture of natural and synthetic terpenes.

In certain embodiments, the terpene is selected from the group consisting of bisabolol, borneol, caryophyllene, carene, camphene, cineol, citronella, eucalyptol, geraniol, guaiol, humulene, isopropyltoluene, isopulegol, linalool, limonene, methyl salicylate, menthol, myrcene, nerolidol, ocimene, pinene, phytol, pulegone, terpinene, terpinolene, thymol, salts thereof, derivatives thereof and mixtures thereof. Each possibility represents a separate embodiment of the invention.

120 distinct terpenes are produced by the genus *Cannabis*, with the relative concentrations of the individual terpenes varying greatly among the 700 distinct strains currently in cultivation. Aside from taste and smell differences between varieties, this helps contribute to the broad diversity of potential medical applications of *Cannabis*.

TABLE 1

Characteristics of exemplary terpenes.

| Terpene | Melting point | LogP | Terpene type |
| --- | --- | --- | --- |
| Beta-caryophyllene | <25° C. | 4.72 | bicyclic sesqui terpene |
| Myrcene | <−10° C. | 4.17 | mono terpene |
| Limonene | −74° C. | 2.38 | cyclic mono terpene |
| Alfa-pinene | −64° C. | 4.37 | bicyclic mono terpene |
| Nerolidol | −75° C. | 4.68 | sesqui terpene |
| Phytol | <25° C. | 7.04 | diterpene |
| Camphene | 51.00° C. | 4.24 | Cyclic mono terpene |
| Terpinene | −31.15° C. | 4.5 | Cyclic mono terpene |
| Carene | 23.00° C. | 4.32 | Bicyclic mono terpene |
| Cineol | 2° C. | 2.7 | Cyclic mono terpene |
| Pulegone | <25° C. | 3.08 | Cyclic mono terpene |
| Citronella | <25° C. | 3.53 | mono terpene |
| Geraniol | −15° C. | 3.47 | mono terpene |
| Menthol | 42° C. | NA | Cyclic mono terpene |
| Borneol | <25° C. | NA | bicyclic mono terpene |
| Linalool | <−20° C. | 2.65 | mono terpene |
| Camphor | Crystals | 2.55 | Bicyclic terpene |
| Terpinen-4-ol | Liquid | 3.26 | Cyclic terpene |
| Thymol | 50° C. | 3.28 | Cyclic Terpene |
| Eugenol | −10° C. | 2.66 | Cyclic terpene |
| Bisabolol | Viscous liquid | 5.07 | Cyclic terpene |
| Methyl salicylate | −9° C. | 2.3 | Cyclic terpene |

Terpene or terpenes mixture useful for solubilizing cannabinoids are liquid at room temperature and have a melting point of below 50° C., below 30° C. or below 25° C. or below 20° C. and a log P octanol/water partition value higher than 2, higher than 3, higher than 3.5 or higher than 4.

In certain embodiments of the pharmaceutical composition, the natural cannabinoid is derived or isolated from an extract of a *Cannabis* plant. In certain embodiments of the composition, the natural terpene is derived or isolated from an extract of a *Cannabis* plant.

In certain embodiments, the a terpene or the mixture of terpenes solubilize a cannabinoid or a mixture of cannabinoid. Each possibility represents a separate embodiment of the invention.

In certain embodiments of the pharmaceutical composition, the weight ratio between the cannabinoid and the emulsifier is about 0.5:1 to about 10:1. In certain embodiments of the pharmaceutical composition, the weight ratio between the cannabinoid and the emulsifier is about 0.5:1 to about 5:1. In certain embodiments of the pharmaceutical composition, the weight ratio between the cannabinoid and the emulsifier is about 0.5:1 to about 4:1. In certain embodiments of the pharmaceutical composition, the weight ratio between the cannabinoid and the emulsifier is about 0.5:1 to about 3:1. In certain embodiments of the pharmaceutical composition, the weight ratio between the cannabinoid and the emulsifier is about 0.5:1 to about 2:1.

The emulsifier component of the formulation can be used to improve cannabinoid solubilization and the self-emulsifying properties of the formulation. Emulsifier components are selected from the group consisting of poly-glycolized glycerides and polyoxyethylene glycerides of medium to long chain mono-, di-, and triglycerides, such as: almond oil PEG-6 esters, almond oil PEG-60 esters, apricot kernel oil PEG-6 esters (Labrafil® M1944CS), caprylic/capric triglycerides PEG-4 esters (Labrafac® Hydro WL 1219), caprylic/capric triglycerides PEG-4 complex (Labrafac® Hydrophile), caprylic/capric glycerides PEG-6 esters (Softigen® 767), caprylic/capric glycerides PEG-8 esters (Labrasol®), castor oil PEG-50 esters, hydrogenated castor oil PEG-5 esters, hydrogenated castor oil PEG-7 esters, 9 hydrogenated castor oil PEG-9 esters, corn oil PEG-6 esters (Labrafil® M 2125 CS), corn oil PEG-8 esters (Labrafil® WL 2609 BS), corn glycerides PEG-60 esters, olive oil PEG-6 esters (Labrafil® M1980 CS), hydrogenated palm/palm kernel oil PEG-6 esters (Labrafil® M 2130 BS), hydrogenated palm/palm kernel oil PEG-6 esters with palm kernel oil, PEG-6, palm oil (Labrafil® M 2130 CS), palm kernel oil PEG-40 esters, peanut oil PEG-6 esters (Labrafil® M 1969 CS), glycerol esters of saturated C8-C18 fatty acids (Gelucire® 33/01), glyceryl esters of saturated C12-C18 fatty acids (Gelucire® 39/01 and 43/01), glyceryl laurate/PEG-32 laurate (Gelucire® 44/14), glyceryl laurate glyceryl/PEG 20 laurate, glyceryl laurate glyceryl/PEG 32 laurate, glyceryl, laurate glyceryl/PEG 40 laurate, glyceryl oleate/PEG-20 glyceryl, glyceryl oleate/PEG-30 oleate, glyceryl palmitostearate/PEG-32 palmitostearate (Gelucire® 50/13), glyceryl stearate/PEG stearate, glyceryl stearate/PEG-32 stearate (Gelucire® 53/10), saturated polyglycolized glycerides (Gelucire® 37/02 and Gelucire® 50/02), triisostearin PEG-6 esters (i.e. Labrafil® Isostearique), triolein PEG-6 esters, trioleate PEG-25 esters, polyoxyl 35 castor oil (Cremophor® EL or Kolliphor® EL), polyoxyl 40 hydrogenated castor oil (Cremophor® RH 40 or Kolliphor® RH40), polyoxyl 60 hydrogenated castor oil (Cremophor® RH60), lecithin, phospholipids and mixtures thereof.

Polyglycolized derivatives and polyoxyethylene esters or ethers derivatives of medium to long chain fatty acids, commercially named Brij and Myrj variety surfactants, and propylene glycol esters of medium to long chain fatty acids, which can be used including caprylate/caprate diglycerides, glyceryl monooleate, glyceryl ricinoleate, glyceryl laurate, glyceryl dilaurate, glyceryl dioleate, glyceryl mono/dioleate, glyceryl caprylate/caprate, medium chain (C8/C10) mono- and diglycerides (Capmul® MCM, Capmul® MCM (L)), mono- and diacetylated monoglycerides, polyglyceryl oleate, polyglyceryl-2 dioleate, polyglyceryl-10 trioleate, polyglyceryl-10 laurate, polyglyceryl-10 oleate, and polyglyceryl-10 mono dioleate, propylene glycol caprylate/caprate (Labrafac® PC), propylene glycol dicaprylate/dicaprate (Miglyol® 840), propylene glycol monolaurate, propylene glycol ricinoleate, propylene glycol monooleate, propylene glycol dicaprylate/dicaprate, propylene glycol dioctanoate, and mixtures thereof.

Sucrose esters surfactants such as sucrose distearate, and polyethylene glycol sorbitan fatty acid esters, which can be used, include PEG-20 sorbitan monolaurate, PEG-20 sorbitan monopalmitate, PEG-20 sorbitan monostearate, and PEG-20 sorbitan monooleate, and TPGS (d-.alpha.-tocopheryl polyethylene glycol 1000 succinate), polysorbate 20 (Tween® 20), polysorbate 80 (Tween® 80), polyethyleneglycol 660 12-hydroxystearate (Solutol® HS-15 or Kolliphor® HS15), sodium lauryl sulfate, and mixtures thereof.

An optional type of a surfactant is amphiphilic surface active molecule that its hydrophobic part comprising at least one moiety of cyclic molecular structure, whereas the cyclic moiety may be of five to nine atoms and atoms may be carbon, nitrogen or oxygen. Example of such surfactants: tocopheryl polyethylene glycol succinate (TPGS), Vit K polyethylene glycol or Coenzyme Q10 polyethylene glycol conjugate, polyethylene glycol or polyglycerol or polysaccharide conjugates of cannabinoids or terpenes, or PEG-Lanoline.

Polyoxyethylene-polyoxypropylene block copolymers, which can be used include poloxamers (108, 124, 182, 183, 188, 212, 217, 238, 288, 331, 338, 335, and 407), and mixtures thereof. Sorbitan fatty acid esters, which can be used, include sorbitan monolaurate, sorbitan monopalmitate, sorbitan monooleate (Span® 20), sorbitan monostearate and sorbitan tristearate, and mixtures thereof.

In certain embodiments, the composition comprises about 5% to about 25% by weight of an emulsifier or a mixture of emulsifiers. In certain embodiments, the pharmaceutical composition comprises about 25% to about 50% by weight of an emulsifier or a mixture of emulsifiers. In certain embodiments, the emulsifier is selected from the group consisting of polysorbate 80, oleoyl polyoxyl-6 glycerides, polyoxyl 35 hydrogenated castor oil, sucrose distearate, tocopherol polyethylene glycol 1000 succinate, lauroyl polyoxyl-32 glycerides, sorbitan monooleate, sucrose tatty acid ester, salts thereof, derivatives thereof, and mixtures of emulsifiers.

In certain embodiments, the pharmaceutical composition comprises (i) about 20% to about 90%, preferably about 30% to about 80%, more preferably about 40% to about 70% by weight of a cannabinoid or a mixture of cannabinoids; (ii) about 5% to about 50%, preferably about 5% to about 35%, more preferably about 5% to about 20% by weight of a terpene or a mixture of terpenes; and (iii) about 5% to about 25% or about 25% to about 50% by weight of an emulsifier or a mixture of emulsifiers. Each possibility represents a separate embodiment of the invention.

In certain embodiments, the pharmaceutical composition comprises or consists of a formulation presented in Table 2. In certain embodiments, the pharmaceutical composition comprises or consists of a formulation presented in Table 3. In certain embodiments, the pharmaceutical composition comprises or consists of a formulation presented in Table 4. In certain embodiments, the pharmaceutical composition comprises or consists of a formulation selected from "Formulation A—With terpenes" and "Formulation B—With terpenes" presented in Table 5. In certain embodiments, the pharmaceutical composition comprises or consists of "CBD29" formulation presented in Table 6. In certain embodiments, the pharmaceutical composition comprises or consists of a formulation presented in Table 7. Each possibility represents a separate embodiment of the invention.

According to the principles of the present invention, and without being limited to any theory or mechanism, in certain embodiments, the Cannabinoid, Terpene and/or Emulsifier in each formulations can be substituted with other Cannabinoid, Terpene and/or Emulsifier in the same or substantially the same % by weight. In certain embodiments, the pharmaceutical composition comprises or consists of a formulation having a Cannabinoid/Terpene/Emulsifier ratio as a formulation in Tables 1 to 4, "Formulation A—With terpenes" and "Formulation B—With terpenes" presented in Table 5, a formulation in Table 6 or a formulation in Table 7. Each possibility represents a separate embodiment of the invention.

In certain embodiments of the pharmaceutical composition, the pharmaceutical composition is liquid at room temperature. In certain embodiments of the pharmaceutical composition, the pharmaceutical composition is semi-solid at room temperature. The term "semi-solid composition" as used herein is intended to mean a non-flowable composition that may be deformed when acted upon by a force. In certain embodiments of the pharmaceutical composition, the pharmaceutical composition is solid at room temperature.

In certain embodiments of the pharmaceutical composition, the pharmaceutical composition self-emulsifies in water at 37° C. within less than 1 hour under light agitation. In certain embodiments of the pharmaceutical composition, the pharmaceutical composition self-emulsifies in water at 37° C. within less than 30 minutes under light agitation. In certain embodiments of the pharmaceutical composition, the pharmaceutical composition self-emulsifies in water at 37° C. within less than 15 minutes under light agitation. In certain embodiments of the pharmaceutical composition, the pharmaceutical composition self-emulsifies in water at 37° C. within less than 5 minutes under light agitation. In certain embodiments of the pharmaceutical composition, the pharmaceutical composition self-emulsifies in water at 37° C. within less than 2 minutes under light agitation. In certain embodiments of the pharmaceutical composition, the pharmaceutical composition self-emulsifies in water at 37° C. within less than 1 minute under light agitation.

In certain embodiments of the pharmaceutical composition, at least 80% by weight of the pharmaceutical composition self-emulsifies within less than 30 minutes. In certain embodiments of the pharmaceutical composition, at least 80% by weight of the pharmaceutical composition self-emulsifies within 5 minutes. In certain embodiments of the pharmaceutical composition, at least 80% by weight of the pharmaceutical composition self-emulsifies within 3 minutes. In certain embodiments of the pharmaceutical composition, at least 80% by weight of the pharmaceutical composition self-emulsifies within 2 minutes. In certain embodiments of the pharmaceutical composition, at least 80% by weight of the pharmaceutical composition self-emulsifies within 1 minute. In certain embodiments of the pharmaceutical composition, at least 80% by weight of the pharmaceutical composition self-emulsifies within 30 seconds. In certain embodiments of the pharmaceutical composition, at least 80% by weight of the pharmaceutical composition self-emulsifies within 10 seconds.

In certain embodiments, the pharmaceutical composition self-emulsifies in an aqueous medium to produce a plurality of particles having a mean particle size in the range of 0.1 to 90 microns. In certain embodiments, the pharmaceutical composition self-emulsifies in an aqueous medium to produce a plurality of particles having a mean particle size in the range of 0.1 to 80 microns. In certain embodiments, the pharmaceutical composition self-emulsifies in an aqueous medium to produce a plurality of particles having a mean particle size in the range of 0.1 to 70 microns. In certain embodiments, the pharmaceutical composition self-emulsifies in an aqueous medium to produce a plurality of particles having a mean particle size in the range of 0.1 to 60 microns. In certain embodiments, the pharmaceutical composition self-emulsifies in an aqueous medium to produce a plurality of particles having a mean particle size in the range of 0.1 to 50 microns. In certain embodiments, the pharmaceutical composition self-emulsifies in an aqueous medium to produce a plurality of particles having a mean particle size in the range of 0.1 to 40 microns. In certain embodiments, the pharmaceutical composition self-emulsifies in an aqueous medium to produce a plurality of particles having a mean particle size in the range of 0.1 to 30 microns. In certain embodiments, the pharmaceutical composition self-emulsifies in an aqueous medium to produce a plurality of particles having a mean particle size in the range of 0.1 to 20 microns. In certain embodiments, the pharmaceutical composition self-emulsifies in an aqueous medium to produce a plurality of particles having a mean particle size in the range of 0.1 to 10 microns.

In certain embodiments, the pharmaceutical composition self-emulsifies in an aqueous medium to produce a plurality of particles having a mean particle size in the range of 1 to 10 microns. In certain embodiments, the pharmaceutical composition self-emulsifies in an aqueous medium to produce a plurality of particles having a mean particle size in the range of 0.1 to 1 microns. In certain embodiments, the pharmaceutical composition self-emulsifies in an aqueous medium to produce a plurality of particles having a mean particle size in the range of 0.01 to 0.1 microns. In certain embodiments, the pharmaceutical composition self-emulsifies in an aqueous medium to produce a plurality of particles having a mean particle size in the range of 0.01 to 10 microns.

In certain embodiments, the pharmaceutical composition self-emulsifies in an aqueous medium to produce a plurality of particles, wherein 50% to 100% of the particles having a particle size in the range of 1 to 10 microns. In certain embodiments, the pharmaceutical composition self-emulsifies in an aqueous medium to produce a plurality of particles, wherein 50% to 100% of the particles having a particle size in the range of 0.1 to 1 microns. In certain embodiments, the pharmaceutical composition self-emulsifies in an aqueous medium to produce a plurality of particles, wherein 50% to 100% of the particles having a particle size in the range of 0.01 to 0.1 microns. In certain embodiments, the pharmaceutical composition self-emulsifies in an aqueous medium to produce a plurality of particles, wherein 50% to 100% of the particles having a particle size in the range of 0.01 to 10 microns.

In certain embodiments of the pharmaceutical composition, the pharmaceutical composition self-emulsifies to produce a plurality of particles, wherein at least 80% of the particles have a size of 30 microns or less. In certain embodiments of the pharmaceutical composition, the pharmaceutical composition self-emulsifies to produce a plurality of particles, wherein at least 80% of the particles have a size of 2 microns or less. In certain embodiments of the pharmaceutical composition, the pharmaceutical composition self-emulsifies to produce a plurality of particles, wherein at least 80% of the particles have a size of 10 microns or less. In certain embodiments of the pharmaceutical composition, the pharmaceutical composition self-emulsifies to produce a plurality of particles, wherein at least 80% of the particles have a size of 5 microns or less. In certain embodiments of the pharmaceutical composition, the pharmaceutical composition self-emulsifies to produce a plurality of particles, wherein at least 80% of the particles have a size of 2 microns or less. In certain embodiments of the pharmaceutical composition, the pharmaceutical composition self-emulsifies to produce a plurality of particles, wherein at least 80% of the particles have a size of 1 microns or less.

In certain embodiments of the pharmaceutical composition, the pharmaceutical composition self-emulsifies to produce a plurality of particles, wherein at least 90% of the particles have a size of 30 microns or less. In certain embodiments of the pharmaceutical composition, the pharmaceutical composition self-emulsifies to produce a plurality of particles, wherein at least 90% of the particles have a size of 2 microns or less. In certain embodiments of the pharmaceutical composition, the pharmaceutical composition self-emulsifies to produce a plurality of particles, wherein at least 90% of the particles have a size of 10 microns or less. In certain embodiments of the pharmaceutical composition, the pharmaceutical composition self-emulsifies to produce a plurality of particles, wherein at least 90% of the particles have a size of 5 microns or less. In certain embodiments of the pharmaceutical composition, the pharmaceutical composition self-emulsifies to produce a plurality of particles, wherein at least 90% of the particles have a size of 2 microns or less. In certain embodiments of the pharmaceutical composition, the pharmaceutical composition self-emulsifies to produce a plurality of particles, wherein at least 90% of the particles have a size of 1 microns or less.

In certain embodiments of the pharmaceutical composition, the pharmaceutical composition self-emulsifies to produce a plurality of particles having a mean particle size of 10 microns or less. In certain embodiments of the pharmaceutical composition, the pharmaceutical composition self-emulsifies to produce a plurality of particles having a mean particle size of 8 microns or less. In certain embodiments of the pharmaceutical composition, the pharmaceutical composition self-emulsifies to produce a plurality of particles having a mean particle size of 6 microns or less. In certain embodiments of the pharmaceutical composition, the pharmaceutical composition self-emulsifies to produce a plurality of particles having a mean particle size of 4 microns or less. In certain embodiments of the pharmaceutical composition, the pharmaceutical composition self-emulsifies to produce a plurality of particles having a mean particle size of 2 microns or less. In certain embodiments of the pharmaceutical composition, the pharmaceutical composition self-emulsifies to produce a plurality of particles having a mean particle size of 1 microns or less.

The pharmaceutical composition of the present invention may be formulated for administration according to any known method. Non-limiting example for administration routs are oral, dermal such as transdermal, intradermal or subcutaneous, and inhalations such as via vaporization, rectal and intraperitoneal. The pharmaceutical composition of the present invention may be introduced by rechargeable or biodegradable polymeric devices or other devices, e.g., patches and pumps, or formulations, which provide for the extended, slow or controlled release of the compound or agent.

According to some embodiments, the pharmaceutical composition is formulated as a modified release composition. The term "modified release composition" herein refers to any composition or dosage form which comprises an active drug and which is formulated to provide a release of active ingredient according to a desired profile, which is different from immediate release. The term comprises composition providing sustained-release, extended-release, prolonged-release, controlled release, delayed release and any combinations of modified release profiles such as extended and delayed-release, of the active ingredient.

The modified release of the active agent such as extended release of delayed release may be accomplished by any known method. The formulation for an extended release may be a single unit dosage form such as tablet, or multiple unit or multi-particulate dosage form such as pellets. Such multiple unit or multi-particulate dosage form may be further formulated into e.g. capsules. Non-limiting examples for extended release systems are matrix system (for example water soluble or water insoluble matrix formers), and reservoir system (such as coated tablets, Osmotic pump systems). Different means for generation of extended release of a drug are described in the art.

The terms "extended release composition" and "sustained release composition" are used herein interchangeably and refer to a composition formulated to release of an active pharmaceutical agent over a prolonged or extended period of time in, such as for example over a period of 8, 12, 16 or 24 hours. The term "delayed release composition" refers to a composition formulated to release discrete portion or portions of drug at a time other than promptly after administration, for examples after passing a particular part of the gastrointestinal tract, e.g. after passing the stomach.

The term "release retardant" as used herein means any excipient that can retard the release of an active pharmaceutical ingredient. Suitable release retardant include polymers, waxes, fatty acids, and others recognized by artisans in the field. In certain embodiments, the release retardant is selected from the group consisting of ethyl cellulose, polyvinylpirrolidone 90, alkyl acrylate, xanthan gum, and any combination thereof. Each possibility represents a separate embodiment of the invention.

In certain embodiments of the pharmaceutical composition, the pharmaceutical composition is formulated for slow release of a cannabinoid or a mixture of cannabinoids upon self-emulsification.

The term "slow release" as used herein applies to any release profile that is other than an immediate release. This includes various terms used interchangeably in the pharmaceutical context such as extended release, sustained release, controlled release and prolonged release.

In certain embodiments of the pharmaceutical composition, the pharmaceutical composition further comprises a release retarding agent or a mixture of a release retarding agents.

The term "release retarding agent" as used herein refers to any agent that prevents or substantially minimizes an immediate release. The term generally refers to a substance, which retard the dosage form disintegration or dosage form dissolution, resulting in slower release profile of the cannabinoids in physiological fluids such as gastro intestinal fluids or simulated gastrointestinal fluids.

In certain embodiments of the pharmaceutical composition, the pharmaceutical composition comprises about 1% to about 20% by weight of a release retarding agent or a mixture thereof. In certain embodiments of the pharmaceutical composition, the pharmaceutical composition comprises about 5% to about 15% by weight of a release retarding agent or a mixture thereof. In certain embodiments of the pharmaceutical composition, the pharmaceutical composition comprises about 6% to about 12% by weight of a release retarding agent or a mixture thereof.

In certain embodiments, the release retarding agent is a high-molecular-weight polymer or a mixture of high-molecular-weight polymer. As used herein, the term "high molecular weight polymer" may refer to a high molecular weight form of a polymer (e.g., a high molecular weight form of an exemplary polymer).

Polymers are used as retarding agents by changing composition matrix consistency and viscosity similar to or by coating that retard the release and/or the disintegration, resulting in slower drug release profile or by forming insoluble or slowly soluble matrix that erodes or dissolves over prolonged time. The term "high-molecular-weight polymer" as used herein refers to a macromolecules composed of repeating small units, obtained by chemical synthesis or natural material extraction or combinations. Water soluble polymers swells or absorbs significant amount of water and produces gel or increase the viscosity due to inter molecular association whereas insoluble polymers swell when in contact with organic solvent such as ethanol.

In certain embodiments, the high-molecular-weight polymer is selected from the group consisting of ethyl cellulose derivatives such as ethyl cellulose or hydroxypeopyl methyl cellulose (HPMC), hydroxyl ethyl cellulose, cellulose phthalate, polyvinylpyrrolidone (PVP), polyvinyl alcohol (PVA), polyvinyl caprolactam—polyvinyl acetate—polyethylene glycol graft copolymer, acrylates and acrilyc polymers, methyl acrylate, methacrylic acid/ethyl acrylate copolymers, alkyl acrylate or cross linked acrylates, natural polysaccharised, such as xanthan gum, guar gum, locust bean gum, gum arabica, pectin, zein, karaya gum, alginate, hyaluronic acid, chitosan, starch, ppolyethylene glycols or polyethylene glycols and polypropylene glycols block copolymers, and mixtures thereof.

In certain embodiments, the viscosity modifying agent is a wax or a mixture of waxes. A wax is a plastic solid at room temperature and a liquid of low viscosity above its melting point. A wax is chemically defined as an ester of a monohydric long-chain fatty alcohol and a long chain fatty acid. In the pharmaceutical literature, the term waxes, fat or lipid have often been used interchangeably and no consistent terminology has been established. Waxes have been used as formulation ingredients in the pharmaceutical industry to increase consistency and viscosity and support matrix formation. The waxes in the current disclosure are used to retard water penetration into the pharmaceutical composition matrix, hence retarding disintegration and/or dissolution.

Waxes are obtained from various sources and are generally classified in to animal, insect, vegetable, mineral and synthetic waxes. Natural waxes: animal waxes:—e.g.—lanoline, spermaceti wax, and wool fat. Insect waxes:—e.g.—bees wax. Vegetable waxes:—e.g.—carnauba wax, japan wax, castor wax, candelilla wax. Synthetic waxes: PEG (molecular weight>700) hydrogenated oil e.g.—hydrogenated cotton seed oil, partially hydrogenated oils.

Waxes may be selected from natural or synthetic waxes, for example waxes that are listed under the FDA list of Rx inactive ingredients: beeswax, candelilla wax, carnauba wax, cetyl esters wax, microcrystalline wax, montan wax, emulsifying wax, white wax, yellow wax. Further waxes may be selected from petrolatum derived waxes, triglyceride waxes, such as hydrogenated castor oil, hydrogenated cotton seed oil, mono, di and triglyceride behenate, long chain polyethylene glycol (PEG) derivatives of fatty acids glycerides or vitamins or cholesterol esters, and mixtures thereof, and plant or animal derived waxes.

Cytochrome P450/P-gp inhibitors include any agent incorporated into the formulation matrix that inhibits presystemic hepatic first pass metabolism (i.e. first pass metabolism), such as d-.alpha.-tocopheryl polyethylene glycol 1000 succinate, anise oil, cinnamon oil, coriander oil, grapefruit oil, lemon oil, orange oil, peppermint oil, ascorbyl palmitate, propyl gallate, piperin, curcumin, resveratrol, and various combinations thereof.

PGP efflux inhibitors include any agent incorporated into the formulation matrix that inhibits PGP induced cellular efflux mechanisms (i.e. MDR), such as polyethoxylated castor oil derivatives, polyoxyethylene sorbitan monooleate, polyoxyethylene glycerides, herbal extracts such as, for example; piperin, ginger liqorice, berberin, and various combinations thereof.

Absorption enhancers are selected from herbal extracts such as piperin, ginger extract, berberin, liquoric, quercetin, resveratrol and vitamin E PEG 1000 succinate (d-.alpha.-tocopheryl polyethylene glycol 1000 succinate or TPGS) and mixtures thereof. These optional components can be used either alone or in combination with other ingredients to improve the chemical and physical properties of the self-emulsifying drug delivery systems.

Furthermore, the dosage form may include viscosity modifying agents, stabilizing agents, fillers, glidants disintegration agent, coating and enteric-coating, microbial preserving agents, as skilled in the art to produce desired dosage form and manufacturability.

Antioxidants include ascorbyl palmitate, butylated hydroxy anisole, butylated hydroxy toluene, propyl gallate, α-tocopherol, and γ-tocopherol, etc. The antioxidants that can be chosen include combinations of two or more agents described above, whereby ascorbyl palmitate and tocopherol provide optimal synergistic effects.

Direct filling of hot melt matrices into hard gelatin or vegetable capsules can be performed in the case of self-emulsifying drug delivery systems. The surfactants and the terpenes acting as dispersing or emulsifying agents for the liberated drug in a finely divided state. The higher surface area of a drug produced in this way facilitates dissolution in the gastrointestinal fluid, especially in the presence of bile salts, lecithin, and lipid digestion mixtures.

In certain embodiments of the pharmaceutical composition, the pharmaceutical composition is formulated for delayed release of a cannabinoid.

The term "delayed release" as used herein applies to any release profile that is other than a release at administration. This includes various terms used interchangeably in the pharmaceutical context such as timed release, specific release and targeted release.

In certain embodiments of the pharmaceutical composition, the pharmaceutical composition is at least partly coated by an enteric-coating agent. In certain embodiments of the pharmaceutical composition, the pharmaceutical composition is coated by an enteric-coating agent. In certain embodiments of the pharmaceutical composition, the pharmaceutical composition is fully coated by an enteric-coating agent. In certain embodiment the pharmaceutical composition is at least partly coated to delay the release and enable prolonged release over few hours.

The term "enteric-coating agent" as used herein applies to any agent that prevents or substantially minimizes exposure to acidic environment, such as the acidic environment in the stomach.

In certain embodiments of the composition, the pharmaceutical composition further comprises about 0% to about 70% by weight of triglycerides, fats, lipids, oils other than essential oils, fatty acids, co-solvents or mixtures thereof. In certain embodiments of the pharmaceutical composition, the pharmaceutical composition further comprises about 0% to about 60% by weight of triglycerides, fats, lipids, oils other than essential oils, fatty acids, co-solvents or mixtures thereof. In certain embodiments of the pharmaceutical composition, the pharmaceutical composition further comprises about 0% to about 50% by weight of triglycerides, fats, lipids, oils other than essential oils, fatty acids, co-solvents or mixtures of triglycerides and/or fatty acids and/or co-solvents. In certain embodiments of the pharmaceutical composition, the pharmaceutical composition further comprises about 0% to about 40% by weight of triglycerides, fats, lipids, oils other than essential oils, fatty acids, co-solvents or mixtures thereof. In certain embodiments of the pharmaceutical composition, the pharmaceutical composition further comprises about 0% to about 30% by weight of triglycerides, fats, lipids, oils other than essential oils, fatty acids, co-solvents or mixtures thereof. In certain embodiments of the pharmaceutical composition, the pharmaceutical composition further comprises about 0% to about 20% by weight of triglycerides, fats, lipids, oils other than essential oils, fatty acids, co-solvents or mixtures thereof. In certain embodiments of the pharmaceutical composition, the pharmaceutical composition further comprises about 0% to about 10% by weight of triglycerides, fats, lipids, oils other than essential oils, fatty acids, co-solvents or mixtures thereof. The term "co-solvent" as used herein refers to any second solvent added in small quantities to enhance the solvent power of the primary solvent.

In certain embodiments, the pharmaceutical composition comprises up to 70% by weight of triglycerides, fats, lipids, oils other than essential oils, fatty acids, co-solvents or mixtures thereof. In certain embodiments of the pharmaceutical composition, the pharmaceutical composition comprises up to 60% by weight of triglycerides, fats, lipids, oils other than essential oils, fatty acids, co-solvents or mixtures thereof. In certain embodiments of the pharmaceutical composition, the pharmaceutical composition comprises up to 50% by weight of triglycerides, fats, lipids, oils other than essential oils, fatty acids, co-solvents or mixtures of triglycerides and/or fatty acids and/or co-solvents. In certain embodiments of the pharmaceutical composition, the pharmaceutical composition comprises up to 40% by weight of triglycerides, fats, lipids, oils other than essential oils, fatty acids, co-solvents or mixtures thereof. In certain embodiments of the pharmaceutical composition, the pharmaceutical composition comprises up to 30% by weight of triglycerides, fats, lipids, oils other than essential oils, fatty acids, co-solvents or mixtures thereof. In certain embodiments of the pharmaceutical composition, the pharmaceutical composition comprises up to 20% by weight of triglycerides, fats, lipids, oils other than essential oils, fatty acids, co-solvents or mixtures thereof. In certain embodiments of the pharmaceutical composition, the pharmaceutical composition comprises up to 10% by weight of triglycerides, fats, lipids, oils other than essential oils, fatty acids, co-solvents or mixtures thereof.

The present invention further provides, in an aspect, a dosage form, comprising or consisting of any one of the compositions described above.

The term "dosage form" denotes any form of the formulation that contains an amount of a cannabinoid or of a mixture of cannabinoids sufficient to achieve at least a partial therapeutic effect with a single administration.

In certain embodiments, the dosage form is an oral dosage form. In certain embodiments, the dosage form is a rectal dosage form. In certain embodiments, the dosage form is a nasal dosage form. In certain embodiment, the dosage form is mucosal dosage form. In certain embodiments, the dosage form is a rectal or vaginal dosage form. In certain embodiments, the dosage form is a topical dosage form. In certain embodiments, the dosage form is an ear dosage form.

In certain embodiments, the dosage form comprises at least about 50 mg of a cannabinoid or a mixture thereof. In certain embodiments, the dosage form comprises at least about 100 mg of a cannabinoid or a mixture thereof. In certain embodiments, the dosage form comprises at least about 200 mg of a cannabinoid or a mixture thereof. In certain embodiments, the dosage form comprises at least about 300 mg of a cannabinoid or a mixture thereof. In certain embodiments, the dosage form comprises at least about 400 mg of a cannabinoid or a mixture thereof. In certain embodiments, the dosage form comprises about 50 mg to about 1,200 mg of a cannabinoid or a mixture thereof. In certain embodiments, the dosage form comprises about 50 mg to about 500 mg of a cannabinoid or a mixture thereof. In certain embodiments, the dosage form comprises about 100 mg to about 400 mg of a cannabinoid or a mixture thereof. In certain embodiments, the dosage form comprises about 100 mg, about 200 mg, about 300 mg, about 400 mg, about 500 mg or about 600 mg of a cannabinoid or a mixture thereof. Each possibility represents a separate embodiment of the invention.

In certain embodiments, the dosage form is formulated as a hard shell capsule, a soft shell capsule, a tablet, a liquid, a syrup or enema or pessaries or ovule. In certain embodiments, the dosage form is granules or pellets delivered in a sachet or filled into capsule or compressed into a tablet. Each possibility represents a separate embodiment of the invention. In certain embodiments, the dosage form is formulated for mucosal delivery. The term "mucosal delivery" refers to the delivery to a mucosal surface, including nasal, pulmonary, vaginal, rectal, urethral, sublingual and buccal delivery. In certain embodiments, the dosage form is formulated as or in a candy, toffee, dragee, chocolate, cookie or lozenge.

According to the principles of the present invention, the self-emulsifying *cannabis* unit dosage form comprises a "*cannabis* active ingredient" (i.e. *Cannabis*-extracted and purified cannabinoid or synthetic cannabinoid or *cannabis* extract), a terpene, and an emulsifier or emulsifiers and optionally inactive ingredients. The advantages of the pharmaceutical composition over known *cannabis* compositions are manifold and include: (a) high dose of cannabinoids in a single unit dosage form (b) self-emulsification in gastro intestinal fluids (c) once or twice daily administration for successful patient compliance.

In an embodiment, the self-emulsifying system when in contact with aqueous mediums such as saline or simulated intestinal fluids or gastro intestinal fluids, at body temperature and mild agitation, forms a fine dispersion with mean particle size below 20 microns, below 10 microns, below 5 microns, below 2 microns or below 1 micro.

In some embodiments, the dosage form is a capsule or tablet or fast disintegrating delivery system or dissolved in mouth dosage form. Capsule formulations may be a hard gelatin or hard vegetable such as HPMC or acid resistant, or soft gelatin type, whereas the pharmaceutical composition is in a liquid, semi-solid, or solid form.

In some embodiments, the dosage form is a capsule or tablet or granules may be entero-coated to avoid stomach release and delay the drug release to upper intestines or to the colon for colonic drug delivery. The entero-coating may be of any type known in pharmaceutical dosage form production.

In an embodiment, optional components of the formulation can include absorption enhancers, such as cytochrome P450 metabolic inhibitors, P-glycoprotein efflux inhibitors and intestinal epithelial cells tight junction temporal openers.

In some embodiments, the dosage form may be granular, whereas the granules are used to feel hard shell capsules or used to press into tablet or suspended to form liquid dosage forms or delivered as is in sachets or in bulk.

In some embodiments, the final dosage form comprises a disintegration retarding agent or dissolution retarding agent and a delayed or slow release is obtained or targeting to various gastro intestinal tract regions.

In some embodiments, a functional inactive ingredient maybe optionally added, such as colorant or antioxidants or glidants or viscosity modifier, or melting point modifier or anti-microbial agent.

In some embodiments, the dosage form has a melting point of above 40° C. and from 40° C. to 80° C., or 40° C. to 70° C. or 42° C. to 60° C. or 44° C. to 50° C. or 38° C. to 40° C., in such a way that the pharmaceutical composition does not liquefy at storage condition, accelerated stability studies and at body temperature.

The present invention further provides, in another aspect, a composition as described above, or a dosage form as described above, for use in a method of treating a cannabinoid-responsive symptom, disease or disorder.

The phrase "cannabinoid-responsive symptom, disease or disorder" as used herein refers to any symptom, disease or disorder which is associated with therapeutic benefit by a cannabinoid, by a mixture of cannabinoids, or by extracts of *Cannabis*.

In certain embodiments, the cannabinoid-responsive symptom, disease or disorder is selected from the group consisting of: pain associated with cancer, neuropathic pain and HIV-associated sensory neuropathy; side effects of chemotherapy including nausea; symptoms of neurology and neurodegenerative diseases such as Huntington's disease, Parkinson's disease, Alzheimer's disease, amyotrophic lateral sclerosis, multiple sclerosis, epilepsy, post-traumatic stress disorder (PTSD), alcohol abuse, bipolar disorder, depression, anorexia nervosa; cancer such as gliomas, leukemia, skin tumors, colorectal cancer; diseases including hepatitis C, methicillin-resistant *Staphylococcus aureus* (MRSA), pruritus, psoriasis, asthma, sickle-cell disease, sleep apnea, digestive diseases, collagen-induced arthritis, atherosclerosis and dystonia and geriatric syndromes. Each possibility represents a separate embodiment of the invention.

In certain embodiments, the present invention provides a pharmaceutical composition of the present invention for use in treating Borderline Personality Disorder (BPD). In certain embodiments, the composition comprises cannabidiol (CBD).

The terms "Borderline Personality Disorder" and "BPD" are used herein interchangeably and refer to prevalent, chronic and debilitating psychiatric disorder as defined in Diagnostic and Statistical Manual of Mental Disorders (DSM) such DSM-5, DSM-4 or equivalent thereof. The BPD is usually diagnosed according to DSM-5 and Structured Clinical Interview for DSM-5—Personality Disorders (SCID-5—PD). BPD is a common mental disorder characterized by a pervasive pattern of emotional lability, impulsivity, interpersonal difficulties, identity disturbances, and disturbed cognition (e.g., dissociative and psychotic-like symptoms). For the purpose of the present invention, the severity or the stage of the disease may be assessed using any known and acknowledged method. According to some embodiments, the stage of disease may be assessed using Borderline Symptom List including 95 questions, (BSL-95), or a shorter list including 23 questions (BSL-23).

According to some embodiments, the treating comprises improvement in scores of one or more of the rating scales selected from the group consisting of Borderline Symptom List 23 (BSL-23); Borderline Symptom List 95 (BSL-95); Brief Psychiatric Rating Scale (BPRS); Hamilton Anxiety (HAM-A); Hamilton Depression (HAM-D); Barratt Impulsiveness Scale (BIS-11); Pittsburgh Sleep Quality Index (PSQI); Columbia-Suicide Severity Rating Scale (C-SSRS); Columbia Non-Suicidal Self-Injury Rating Scale; Sheehan Disability Scale (SDS); Fagerstrom test for nicotine dependence (FTND); Pain Catastrophizing symptoms questionnaire (PCS); and Zanarini Rating Scale for BPD (ZAN-BPD). According to some embodiment, treating comprises improvement in score in at least one of the above rating scales, indices or tests.

According to one embodiment, treating comprises improvement in a score obtained upon rating using BSL-23 rating scale. According to another embodiment, treating comprises or characterized by improvement in scores obtained upon rating using Columbia-Suicide Severity Rating Scale (C-SSRS) or Columbia Non-Suicidal Self-Injury Rating Scale. According to another embodiment, treating comprises improving depression symptoms associated with BPD as assessed by Hamilton Depression (HAM-D). According to some embodiments, treating comprises improvement in scores as assessed in two or more of the above scales, indices or tests.

According to the present invention, the term "improvement" is defined as reduction in the severity of one or more symptoms associated with BPD in comparison to the base level, as assessed by any one of the abovementioned tests or scales. The term improvement in score may be reflected in an increase in scores or in a decrease in scores as a dependence of the rating scale and scoring method. In any case, this term refers to improvement in symptoms as would be clear to any person skilled in the art. The term "base level" refers the score obtained in the relevant rating scale, index or test prior to beginning of the treatment, e.g. a day before beginning of the treatment, or short period before treatment.

According to some embodiments, treating comprises improvement of at least 5% in the rating scale scored in comparison to the base level. According to another embodiment, the improvement is of at least 10%, at least 15%, at least 20%, at least 25% or at least 30% in scores from the base level. According to other embodiment, the improvement is of 40%, 50%, 60%, 70%, 80% 90%, 100% or more from the base level. According to some embodiment, the treating comprises improvement of 2, 3, 4, or 5 time in comparison to the base level.

According to some embodiment, the improvement is achieved after certain period of time. According to one embodiment, the improvement is achieved after 1, 2, 3, 4, 5, 6, 8 or 10 weeks or more. According to some embodiment, the improvement is estimated and/or observed after at least 1 week of treatment. According to another embodiment, the improvement is estimated and/or observed after at least 2 weeks, or after at least 4 weeks of treatment. According to another embodiment, the improvement is estimated and/or observed after at least 6 weeks or treatment.

According to some embodiments, treating comprises improvement of at least 10% in BSL-23 rating scale score in comparison to the base scale, as estimated after at least 2 weeks of treatment. According to another embodiment, the treating comprises improvement of at least 15% or at least 20% in BSL-23 rating scale. According to such embodiment, the improvement is estimated and/or observed after at least 4 or at least 6 weeks of treatment.

According to other embodiments, the treating comprises improvement of at least 5% or at least 10% in C-SSRS score or Columbia Non-Suicidal Self-Injury Rating Scale score after the treatment of at least 4 weeks, in comparison to the base level. According to another embodiment, the treating comprises improvement of at least 15% or at least 20% in BSL-23 rating scale. According to such embodiment, the improvement is estimated after at least 4 or at least 6 weeks of treatment.

According to some embodiments, treating comprises improvement in score of 2, 3, 4, or 5 rating scales defined above. According to one embodiment, treating comprises improvement in BSL-23 rating scale score and in score of one or more rating scales selected from the group consisting of BPRS; HAM-A; HAM-D; BIS-11; PSQI; C-SSRS; Columbia Non-Suicidal Self-Injury Rating Scale; SDS; FTND; PCS; and ZAN-BPD.

Many BPD patients consume psychotropic medications to alleviate the symptoms of the disorder. According to any one of the above embodiments, treating comprises a decrease in use of psychotropic drugs. According so some embodiment, the psychotropic drugs are selected from the group consisting of anxiolytics, antidepressants, antipsychotics, and mood stabilizers drugs. According to some embodiments, the antipsychotic drugs are selected from typical antipsychotic such as haloperidol and flupenthixol; atypical antipsychotics such as topiramate, olanzapine, ziprasidone and carbamazepine; mood stabilizers such as valproate, lamotrigine, topiramate; antidepressants, for examples SSRIs, tricyclic and tetracyclic antidepressants, and Serotonin-norepinephrine reuptake inhibitor (SNRIs), anxiolytics such as barbiturates, benxodiazepines and carbamates. Examples of antidepressants are amithiptyline, mianserin, fluoxetine, fluvoxaminer and phenelzine.

According to some embodiments, decrease in use of the psychotropic medications comprises decrease in a consumed dose of said medications. According to another embodiment, decrease in use comprises decrease in an administration frequency of the psychotropic drugs. According to a further embodiment, decrease in use comprises both decrease in the dose and frequency of administration of said drugs.

According to some embodiment, decrease in use of the psychotropic medications comprises decrease of at least 10%, 20%, 30%, 50% of the consumed daily dose of the medication. According to another embodiment, the decrease comprises decrease of at least 10%, 20%, 30%, 50% of the consumed weakly dose of the medication. According to some embodiments, the decrease comprises cessation of the administration of the medication.

According to some embodiments, decrease in use of the psychotropic medications comprises decrease of at least 10%, 20%, 30%, 50% in administration frequency of the psychotropic drugs.

According to any one of the above embodiments, the pharmaceutical composition for use according to the present invention, comprises at least 20% by weight CBD. According to other embodiments, the pharmaceutical composition comprises at least 30% by weight, at least 40% by weight, at least 50% by weight at least 60% by weight, at least 70% by weight, at least 80% by weight or at least 90% by weight of CBD. According to another embodiment, the pharmaceutical composition comprises CBD in the range of about 20% by weight to about 90% by weight, about 30% by weight to about 80% by weight, about 40% by weight to about 70% by weight or about 50 to about 60% by weight. According to some embodiments, the pharmaceutical composition comprises about 40% by weight to about 80% by weight, about 50% by weight to about 70% by weight, or about 55% by weight to about 65% by weight of CBD. According to any one of the above embodiment, the pharmaceutical composition comprises one or more cannabinoids other than CBD. According to some embodiments, the pharmaceutical composition comprises from about 5% by weight to about 35% by weight of one or more terpenes. According to some embodiments, the pharmaceutical composition comprises about 5% by weight to about 30 wt %, about 7% by weight to about 25% by weight or about 10 to about 20% by weight of terpenes. According to some embodiments, the pharmaceutical composition comprises the an emulsifier. According to some embodiments, the emulsifier is present in the pharmaceutical composition in the range of about 5% by weight to about 50% by weight. According to other embodiment, the pharmaceutical composition comprises from about 7% by weight to about 40% by weight, about 8% by weight to about 30% by weight, about 9% by weight to about 25% by weight, about 10% by weight to about 20% by weight of emulsifier. According to other embodiments, the pharmaceutical composition comprises about 5% by weight to about 25% by weight, about 7% by weight to about 20% by weight, about 10% by weight to about 15% by weight of emulsifier.

According to some embodiments, the pharmaceutical composition comprises from about 30% by weight to about 60% by weight of CBD, about 5% to about 30% by weight of one or more terpenes or a mixture of terpenes; and from about 20% by weight to about 60% by weight of emulsifiers. According to some embodiments, the pharmaceutical composition comprises from about 40% by weight to about 55% by weight of CBD. According to other embodiments, the pharmaceutical composition comprises from about 7% by weight to about 20% by weight terpenes. According to one embodiment, the pharmaceutical composition comprises from about 30% by weight to about 50% by weight of emulsifiers. According to one particular embodiment, the pharmaceutical composition comprises from about 40% by weight to about 55% by weight of CBD, from about 5% by weight to about 20% by weight terpenes and from about 30% by weight to about 50% by weight emulsifiers. According to any one of the above embodiment, the pharmaceutical composition further comprises THC. According to some such embodiments, the CBD:THC weight ratio is at least 10:1, 15:1 or 20:1. According to some embodiments, the pharmaceutical composition is formulated as capsules. According to some embodiments, the capsules comprises 100, 200, 300, 400, 500 or 600 mg of CBD. According to any one of the above embodiment, the treating comprises administering CBD in the amount of about 100, 200, 300, 400, 500, 600, 800, or 1000 mg/day. The administration comprise administering the pharmaceutical composition in one dose a day or in several doses, e.g. 2, 3, 4, 5, or 6 doses a day.

According to some embodiments, the selected terpenes are of the alerting type, such as Limonene, alfa and beta pinene, orange terpenes, thymol, isoborneol and isoeugenol, and not the sedating type terpenes, such as myrcene, linalool, linalyl acetate, alfa terpineol, citronellal, sandalwood, lavender, valerian and neroli oils. Example of alerting *cannabis* strains are Harlequin™, Charlotte's Web™, ACDC™, Avi-dekel™ and Remedy™.

According to a further aspect, the present invention provides a method of treating a cannabinoid-responsive symptom, disease or disorder, the method comprises administering a composition according to the present invention.

According to another aspect, the present invention provised use of a composition of the present invention for preparing a pharmaceutical or medicinal or veterinary composition for use in treating a cannabinoid-responsive symptom, disease or disorder.

In some embodiments, a cannabinoid responsive disorder is selected from disorders responsive to treatment with *cannabis* including but not limited to pain associated with cancer, neuropathic pain and HIV-associated sensory neuropathy; side effects of chemotherapy including nausea and pain; symptoms of neurology and neurodegenerative diseases such as Huntington's disease, Parkinson's disease, Alzheimer's disease, amyotrophic lateral sclerosis, multiple sclerosis, epilepsy, post-traumatic stress disorder (PTSD), alcohol abuse, bipolar disorder, depression, anorexia nervosa; cancer such as gliomas, leukemia, skin tumors, colorectal cancer; diseases including hepatitis C, methicillin-resistant *Staphylococcus aureus* (MRSA), pruritus, psoriasis, asthma, sickle-cell disease, sleep apnea, digestive diseases, collagen-induced arthritis, atherosclerosis, dystonia, inflammatory bowel diseases (IBD) and geriatric syndromes.

Indications are those that are treated by pure cannabinoids or benefiting from high dose of cannabinoids or by an extract of cannabinoids or by an extract of high CBD and low THC ratio, to avoid psychotic effects. Such indication for example are graft versus host disease (GVHD), inflammatory bowel diseases (IBD), epilepsy, psychiatric indications such as schizophrenia and borderline personality disorders (BPD) and opioid addiction withdrawal syndrome.

The present invention further provides, in another aspect, a method of treating borderline personality disorder (BPD) in a subject in need thereof, comprising administering a composition comprising therapeutically-effective amount of cannabidiol (CBD) to the subject.

In an embodiment, the pharmaceutical composition is used to treat psychiatric disorders; borderline personality disorder, anxiety, impulsivity, instability, suicidal, self-injury, anhedonia behavior.

In certain embodiments, a self-emulsifying pharmaceutical composition or dosage form according to the present invention is for use in treating Borderline Personality Disorder (BPD).

In certain embodiments, the treating comprises improvement in scores of one or more of the rating scales selected from the group consisting of Borderline Symptom List 23 (BSL-23); Borderline Symptom List 95 (BSL-95); Brief Psychiatric Rating Scale (BPRS); Hamilton Anxiety (HAM-A); Hamilton Depression (HAM-D); Barratt Impulsiveness Scale (BIS-11); Pittsburgh Sleep Quality Index (PSQI); Columbia-Suicide Severity Rating Scales (C-SSRS); Columbia Non-Suicidal Self-Injury Rating Scale; Sheehan Disability Scale (SDS); Fagerstrom test for nicotine dependence (FTND); Pain Catastrophizing symptoms questionnaire (PCS); and Zanarini Rating Scale for BPD (ZAN-BPD). In certain embodiments, the treating comprises improvement in BSL-23 rating scale scores.

In certain embodiments, the improvement comprises improvement of at least 5% in the rating scale scored in comparison to the base level. In certain embodiments, the improvement comprises improvement of at least 20% in the rating scale scores in comparison to the base level. In certain embodiments, the improvement is estimated after at least 2 weeks of the treatment. In certain embodiments, improvement is estimated after at least 6 weeks of treatment.

In certain embodiments, the treating comprises improvement of at least 10% in BSL-23 rating scale scores in comparison to the base level, as estimated after at least 4 weeks of treatment. In certain embodiments, the treating comprises improvement of at least 10% in C-SSRS or Columbia Non-Suicidal Self-Injury Rating Scale scores after the treatment of at least 4 weeks, in comparison to the base level. In certain embodiments, the treating comprises improvement in BSL-23 rating scale scores and in scores of one or more rating scales selected from the group consisting of BPRS; HAM-A; HAM-D; BIS-11; PSQI; C-SSRS; Columbia Non-Suicidal Self-Injury Rating Scale; SDS; FTND; PCS; and ZAN-BPD.

In certain embodiments, the treating comprises a decrease in use of psychotropic drugs. In certain embodiments, the psychotropic drugs are selected from the group consisting of anxiolytics, antidepressants, antipsychotics, and mood stabilizers drugs.

In certain embodiments, the decrease in use comprises decrease in a dose and/or in an administration frequency of the psychotropic drugs. In certain embodiments, decrease in use comprises decrease of at least 10% in a weekly dose of said drug.

In certain embodiments, the pharmaceutical composition comprises cannabidiol (CBD). In certain embodiments, the pharmaceutical composition comprises at least 20% by weight CBD. In certain embodiments, the pharmaceutical composition comprises CBD in the range of about 30% by weight to about 80% by weight. In certain embodiments, the pharmaceutical composition comprises from about 5% by weight to about 35% by weight of one or more terpenes.

In certain embodiments, the pharmaceutical composition further comprises one or more cannabinoids other than CBD. In certain embodiments, the one or more cannabinoids are selected from the group consisting of Cannabidiolic acid (CBDA), Tetrahydrocannabinol (THC), Tetrahydrocannabinolic acid (THCA), Cannabigerol (CBG), Cannabichromene (CBC), Cannabinol (CBN), Cannabielsoin (CBE), iso-Tetrahydrocannabimol (iso-THC), Cannabicyclol (CBL), Cannabicitran (CBT), Cannabivarin (CBV), Tetrahydrocannabivarin (THCV), Cannabidivarin (CBDV), Cannabichromevarin (CBCV), Cannabigerovarin (CBGV) and Cannabigerol Monomethyl Ether (CBGM), salts thereof, and derivatives thereof.

In certain embodiments, the pharmaceutical composition comprises from about 20% by weight to about 90% by weight of cannabinoids. In certain embodiments, the pharmaceutical composition comprises tetrahydrocannabinoid (THC). In certain embodiments, the weight ratio of CBD to THC (CBD:THC ratio) is at least 8:1. In certain embodiments, the CBD:THC weight ratio is at least 20:1. In certain embodiments, the emulsifier is present in the range of about 5% by weight to about 50% by weight.

In an embodiment, the pharmaceutical composition is used to treat inflammatory bowel diseases, Graft-versus-host disease (GVHD), and any medical *cannabis* treatment requires large dose of *cannabis* or cannabinoids or CBD.

The present invention further provides, in an aspect, a method for producing a composition as described above or a dosage form as described above, comprising the step of melting and mixing the cannabinoid, the terpene, the emulsifier and optionally the release retarding agent, and further optionally comprising the steps of cooling the mixture; filling a hard or soft shell or capsule with the mixture; at least partly coating the mixture; and any combination thereof.

The terms "treat," "treating," or "treatment" as used herein, include reducing, alleviating, abating, ameliorating, relieving, or lessening a symptom associated with either a chronic or acute therapeutic scenario treatable with *cannabis* extract or cannabinoids. In some embodiments, the term includes, but are not limited to, alleviation or amelioration of one or more symptoms or parameters associated with a disease, and in particular symptoms or parameters associated with BPD, such as improvement in parameters as assessed various rating scales, tests or indices.

The aspects and embodiments provided herein have been described in an illustrative manner, and it is to be understood that the terminology used is intended to be in the nature of words of description rather than of limitation.

Many modifications and variations are possible in light of the above teachings. It is, therefore, to be understood that within the scope of the appended claims, the invention can be practiced otherwise than as specifically described.

The present disclosure is illustrated in detail below with reference to examples, but is not to be construed as being limited thereto.

Citation of any document herein is not intended as an admission that such document is pertinent prior art, or considered material to the patentability of any claim of the present disclosure. Any statement as to content or a date of any document is based on the information available to applicant at the time of filing and does not constitute an admission as to the correctness of such a statement.

EXAMPLES

Example 1

TABLE 2

Exemplary high-concentration cannabinoid extract formulations, according to the present invention.

| Ingredient | Function | F001 % w/w | F002 % w/w | F003 % w/w | F004 % w/w | F005 % w/w | F006 % w/w | F007 % w/w | F008 % w/w |
|---|---|---|---|---|---|---|---|---|---|
| Cannabis extract | Cannabis extract | 80 | 80 | 80 | 90 | 90 | 90 | 60 | 60 |
| Polysorbate 80 | Emulsifier | 10 | | | 5 | | | | |
| Labraphil M1954 | Emulsifier | | | 10 | | | | | |
| Cremophor EL | Emulsifier | 10 | 10 | | 5 | 5 | | 10 | |
| Sucrose ester | Emulsifier | | 10 | 10 | | 5 | 5 | 10 | 10 |
| TPGS | Emulsifier | | | | | | 5 | | 10 |
| Gelucire 44/14 | Emulsifier | | | | | | | | |
| Microcrystalline wax | Viscosity modifier | | | | | | | 20 | 20 |
| Glyceryl dibehenate | Viscosity modifier | | | | | | | | |
| Hydrogenated castor oil wax MP80 | Viscosity modifier | | | | | | | | |
| Ethyl cellulose | Polymer release retardant | | | | | | | | |
| Polyvinylpirrolidone 90 | Polymer release retardant | | | | | | | | |
| Alkyl acrilate | Polymer release retardant | | | | | | | | |
| Xanthan gum | Polymer release retardant | | | | | | | | |
| Total (%w/w) | | 100% | 100% | 100% | 100% | 100% | 100% | 100% | 100% |
| Self-emulsification (score) | | 3 | 3 | 3 | 3 | 3 | 3 | 3 | 3 |
| Grade | | B | B | B | B | B | B | B | B |
| Mean particle size | | <2μ | <2μ | <2 μ | <2 μ | <2 μ | <2 μ | <2 μ | <2 μ |
| Largest detected size | | <10μ | <10μ | <10 μ | <10μ | <10μ | <10μ | <10μ | <10μ |
| Mean size post disintegration | | | | | | | | | |
| Grade post dissolution | | | | | | | | | |
| C-E-V-P | | 80-20-0-0 | 80-20-0-0 | 80-20-0-0 | 90-10-0-0 | 90-10-0-0 | 90-10-0-0 | 60-20-20-0 | 60-20-20-0 |

| Ingredient | Function | F009 %w/w | F010 % w/w | F011 % w/w | F012 % w/w | F013 % w/w | F014 % w/w | F015 % w/w | F016 % w/w |
|---|---|---|---|---|---|---|---|---|---|
| Cannabis extract | Cannabis extract | 60 | 60 | 60 | 70 | 85 | 70 | 80 | 80 |
| Polysorbate 80 | Emulsifier | | | | | | | | |
| Labraphil M1954 | Emulsifier | | 5 | | | | | | |
| Cremophor EL | Emulsifier | | | | | | | | |
| Sucrose ester | Emulsifier | | 5 | 4 | 4 | 4 | 4 | 6 | 6 |
| TPGS | Emulsifier | 10 | 5 | 6 | 5 | 4 | 6 | 6 | 6 |
| Gelucire 44/14 | Emulsifier | 10 | | | | | | | |
| Microcrystalline wax | Viscosity modifier | | 10 | 18 | 15 | | | | |
| Glyceryl dibehenate | Viscosity modifier | | 15 | | | | 12 | | |

TABLE 2-continued

Exemplary high-concentration cannabinoid extract formulations, according to the present invention.

| | | | | | | | | | |
|---|---|---|---|---|---|---|---|---|---|
| Hydrogenated castor oil wax MP80 | Viscosity modifier | 20 | | | | | | | |
| Ethyl cellulose | Polymer release retardant | | | 8 | 4 | 4 | 4 | 4 | |
| Polyvinylpirrolidone 90 | Polymer release retardant | | | | | | | 4 | 4 |
| Alkyl acrilate | Polymer release retardant | | | 4 | 2 | 3 | | | 4 |
| Xanthan gum | Polymer release retardant | | | | | | 4 | | |
| Total (% w/w) | | 100% | 100% | 100% | 100% | 100% | 100% | 100% | 100% |
| Self-emulsification (score) | | 3 | 3 | n.a.* | n.a.* | n.a.* | n.a.* | n.a.* | n.a.* |
| Grade | | B | B | | | | | | |
| Mean particle size | | <2μ | <2μ | | | | | | |
| Largest detected size | | <10μ | <10μ | | | | | | |
| Mean size post disintegration | | | | <2μ | <2μ | <2μ | <2μ | <2μ | <2μ |
| Grade post dissolution | | | | B | B | B | B | B | B |
| C-E-V-P | | 60-20-20-0 | 60-15-25-0 | 60-10-18-12 | 70-9-15-6 | 85-8-0-7 | 70-10-12-8 | 80-12-0-8 | 80-12-0-8 |

*n.a.—not applicable.

The self-emulsifying compositions described herein in the "Examples" section were all testes for stability after self-emulsification upon mixing with simulated intestinal fluids at 37° C., and found to be stable for at least 24 hours post emulsification.

The *cannabis* extract composition in Table 2 was produced by an ethanol extraction of decarboxylated plant material, and comprises about 40% by weight THC, about 40% by weight CBD, and about 4% by weight terpenes.

For determining the "Largest detected size", the tested formulation is mixed 1:5 with distilled water at room temperature and slightly rotated until emulsification occur. A drop is then placed on bearing glass and covered with top glass, and the sample is immediately examined with light microscope magnification ×200 with calibrated scale.

For determining the "Mean particle size", the DLS method was performed with Malvern Sizer™. The sample is diluted 1:200 with distilled water and slightly rotated. The test was performed according to Malvern instruction, and further dilutions were performed as needed and indicated by the instrument. The "mean particle size" was calculated based on the number distribution of all particles.

The scoring for all compositions provided by the present invention in the self-emulsification test, performed at 37° C. in water under light agitation, was as indicated: 1—non self-emulsifying, 2—self-emulsifying within 30 to 120 seconds, and 3—self-emulsifying within 30 seconds.

The grading of self-emulsification for all compositions provided by the present invention was adopted from Gupta et al. (Int. J. of Pharm. & Life Sci. (IJPLS), 2011, Vol. 2, Issue 3, pages 633-639), and was as indicated: Grade A—rapidly forming emulsion having a clear or bluish appearance, Grade B—rapidly forming, slightly less clear emulsion, having a bluish white appearance, Grade C—fine milky emulsion, formed within 2 minutes, Grade D—dull, greyish white emulsion, having slightly oily appearance, that is slow to emulsify (more than 2 minutes), and Grade E—formulation exhibiting either poor or minimal emulsification, with large oil globules present on the surface.

Formulation F011-F016 comprise release retarding polymers, thus it is not possible to perform the regular "self-emulsification" tests. Only upon disintegration of the capsule and the disintegration and dissolution of formulation, one can test what types of particles (if at all) are produced, typically within two minutes. Therefore, while the results of self-emulsification of formulations F001-F010 relate to immediate emulsification, the post-dissolution results of self-emulsification is provided in case of formulations containing release retarding agents.

Example 2

TABLE 3

Exemplary high-concentration pure cannabinoid formulations, according to the present

| | Function | CBD02 % w/w | CBD03 % w/w | CBD04 % w/w | CBD05 % w/w | CBD08 % w/w | CBD09 % w/w | CBD10 % w/w |
|---|---|---|---|---|---|---|---|---|
| CBD (99.9%) | Cannabinoid | 54.36 | 67.14 | 60.55 | 56.41 | 49.77 | 50.86 | 45.71 |
| Pinene | Terpene | 5.37 | 4.24 | 4.59 | 4.27 | 3.83 | 8.20 | 7.80 |
| Cineol | Terpene | 2.68 | 2.12 | 1.83 | 2.56 | 2.30 | 4.10 | 3.90 |
| Methyl salicylate | Terpene | | | | | | | |

TABLE 3-continued

Exemplary high-concentration pure cannabinoid formulations, according to the present

| | Function | | | | | | | |
|---|---|---|---|---|---|---|---|---|
| Eucalyptus oil Cineol 60% | Terpene mixture | | | | | | | |
| Rosmarinus oil Pinen >60% | Terpene mixture | | | | | | | |
| TPGS | Emulsifier | | | 17.43 | 9.40 | 9.65 | | 15.60 |
| Tween 80 | Emulsifier | | 13.78 | | | | 11.16 | 11.70 |
| Span 80 | Emulsifier | | | | 10.26 | 13.78 | | |
| Cremophor EL | Emulsifier | 18.79 | 12.72 | | 17.09 | | | 15.29 |
| Surphope 1811 | Emulsifier | 18.79 | | 15.60 | | 20.67 | | |
| Labraphil M1954 | Emulsifier | | | | | | 10.91 | |
| Gelucire 44/14 | Emulsifier | | | | | | 14.77 | |
| | | | | | | | | |
| Total (% w/w) | | 100% | 100% | 100% | 100% | 100% | 100% | 100% |
| Self-emulsification (score) | | 2 | 2 | 2 | 3 | 3 | 2 | 3 |
| Grade | | D | D | D | C | C | D | B |
| Largest detected size | | <20μ | <20μ | <20μ | <15μ | <10μ | <25μ | <25μ |
| Mean particle size | | <5μ | <2μ | <2μ | <2μ | <1μ | <5μ | <5μ |
| C-T-E | | 54-8-38 | 67-6-27 | 60-6-34 | 56-7-37 | 50-6-44 | 50-12-38 | 45-12-43 |

| | Function | CBD11 % w/w | CBD12 % w/w | CBD13 % w/w | CBD14 % w/w | CBD15 % w/w | CBD16 % w/w |
|---|---|---|---|---|---|---|---|
| CBD (99.9%) | Cannabinoid | 42.55 | 52.88 | 49.78 | 46.09 | 40.82 | 43.73 |
| Pinene | Terpene | 7.09 | | | | | |
| Cineol | Terpene | 3.55 | | | | | |
| Methyl salicylate | Terpene | | | | | | 17.56 |
| Eucalyptus oil Cineol 60% | Terpene mixture | | | 10.42 | 12.53 | 13.27 | |
| Rosmarinus oil Pinen >60% | Terpene mixture | | 12.27 | | | | |
| TPGS | Emulsifier | 21.28 | 21.15 | 16.00 | 17.17 | 20.41 | 17.00 |
| Tween 80 | Emulsifier | | 13.71 | | | | 9.48 |
| Span 80 | Emulsifier | 13.05 | | | 6.57 | 8.02 | 5.20 |
| Cremophor EL | Emulsifier | 12.48 | | | 17.63 | | 2.11 |
| Surphope 1811 | Emulsifier | | | 23.81 | | 8.02 | 4.92 |
| Labraphil M1954 | Emulsifier | | | | | 9.48 | |
| Gelucire 44/14 | Emulsifier | | | | | | |
| | | | | | | | |
| Total (% w/w) | | 100% | 100% | 100% | 100% | 100% | 100% |
| Self-emulsification (score) | | 3 | 3 | 3 | 2 | 3 | 2 |
| Grade | | B | B | D | D | C | C |
| Largest detected size | | <20μ | <8μ | <25μ | <15μ | <15μ | <30μ |
| Mean particle size | | <5μ | <1μ | <5μ | <5μ | <2μ | <2μ |
| C-T-E | | 42-11-47 | 53-12-35 | 50-10-40 | 46-12-42 | 41-12-47 | 44-18-38 |

| | Function | CBD17 % w/w | CBD18 % w/w | CBD20 % w/w | CBD21 % w/w | CBD22 % w/w | CBD23 % w/w | CBD24 % w/w | CBD25 % w/w |
|---|---|---|---|---|---|---|---|---|---|
| CBD (99.9%) | Cannabinoid | 41.21 | 39.81 | 48.28 | 52.00 | 40.29 | 48.33 | 45.47 | 47.75 |
| Pinene | Terpene | | | | 6.00 | | 14.17 | 5.88 | |
| Cineol | Terpene | | | | 6.00 | | | 5.88 | |
| Caryophyllene | Terpene | | | | | 10.4 | | 5.88 | |
| Myrcene | Terpene | | | | | | | | |
| Limonene oil | Terpene | | | | | | | | 13.47 |
| Menthol crystals | Terpene | | | 14.18 | | | | | |
| Thyme oil | Terpene | 13.55 | | | | | | | |
| Clove oil 79% Eugenol | Terpene mixture | | 14.75 | | | | | | |
| Eucalyptus oil Cineol 60% | Terpene mixture | | | | | | | | |
| TPGS | Emulsifier | 17.64 | 17.03 | 22.22 | 15.00 | 9.65 | 8.71 | 5.88 | 14.37 |
| Tween 80 | Emulsifier | 9.17 | 8.57 | 15.33 | | | | | |
| Span 80 | Emulsifier | 8.33 | 7.07 | | | 9.59 | | | |
| Cremophor EL | Emulsifier | 10.09 | 8.57 | | 15.00 | 8.67 | 6.51 | 5.88 | 13.99 |
| Surphope 1811 | Emulsifier | | 4.20 | | | 21.38 | 21.97 | | 10.4 |

TABLE 3-continued

Exemplary high-concentration pure cannabinoid formulations, according to the present

| Labraphil M1954 | Emulsifier | | | | 0 | | | | |
|---|---|---|---|---|---|---|---|---|---|
| Total (% w/w) | | 100% | 100% | 100% | 100% | 100% | 100% | 100% | 100% |
| Self-emulsification (score) | | 3 | 2 | 3 | 2 | 3 | 2 | 2 | 2 |
| Grade | | C | D | D | C | C | D | C | D |
| Largest detected size | | <12μ | <20μ | <10μ | <30μ | <25μ | <30μ | <30μ | <20μ |
| Mean particle size | | <2μ | <5μ | <2μ | <2μ | <2μ | <10μ | <5μ | <5μ |
| C-T-E | | 41-14-45 | 40-15-45 | 48-14-38 | 52-12-36 | 40-10-46 | 48-14-37 | 45-18-12 | 47-13-39 |

Example 3

TABLE 4

Exemplary high-concentration pure cannabinoid formulations, according to the present invention.

| | Function | FTHC % w/w | FCBC % w/w | FCBV % w/w | FCBG % w/w | FCBN % w/w | FCBDA % w/w |
|---|---|---|---|---|---|---|---|
| Tetrahydrocannabinol (THC) | Cannabinoid | 60 | 0 | 0 | 0 | 0 | 0 |
| Cananbichrome (CBC) | Cannabinoid | 0 | 60 | 0 | 0 | 0 | 0 |
| Cannabivarin (CBV) | Cannabinoid | 0 | 0 | 60 | 0 | 0 | 0 |
| Cannabigerol (CBG) | Cannabinoid | 0 | 0 | 0 | 60 | 0 | 0 |
| Cannabinol (CBN) | Cannabinoid | 0 | 0 | 0 | 0 | 60 | 0 |
| Cannabidiolic acid (CBDA) | Cannabinoid | 0 | 0 | 0 | 0 | 0 | 60 |
| Pinene | Terpene | 5 | 5 | 5 | 5 | 5 | 5 |
| Cineol | Terpene | 5 | 5 | 5 | 5 | 5 | 5 |
| Caryophyllene | Terpene | 5 | 5 | 5 | 5 | 5 | 5 |
| TPGS | Emulsifier | 9 | 9 | 9 | 9 | 9 | 9 |
| Cremophor EL | Emulsifier | 8 | 8 | 8 | 8 | 8 | 8 |
| Surphope 1811 | Emulsifier | 8 | 8 | 8 | 8 | 8 | 8 |
| Total (% w/w) | | 100 | 100 | 100 | 100 | 100 | 100 |
| Self-emulsification (score) | | 3 | 3 | 3 | 3 | 3 | 3 |
| Grade | | C | C | C | C | C | C |
| C-T-E | | 60-15-25 | 60-15-25 | 60-15-25 | 60-15-25 | 60-15-25 | 60-15-25 |

Example 4

TABLE 5

Exemplary high-concentration pure cannabinoid formulations, according to the present invention.

| | Function | Formulation A-No terpenes mg | Formulation A-With terpenes mg | Formulation B-No terpenes mg | Formulation B-With terpenes mg |
|---|---|---|---|---|---|
| CBD (99.9%) | Cannabinoid | 57.89 | 47.83 | 56.31 | 47.15 |
| Pinene | Terpene | | 10.43 | | 9.76 |
| Cineol | Terpene | | 6.96 | | 6.50 |
| TPGS | Emulsifier | 18.95 | 15.65 | | |
| Span 80 | Emulsifier | | | 24.27 | 20.33 |
| Surphope 1811 | Emulsifier | 23.16 | 19.13 | 19.42 | 16.26 |
| Total (mg) | | 100 | 100 | 100 | 100 |
| Self-emulsification (score) | | 1 | 3 | 1 | 3 |
| Grade | | Not self-emulsifying | C | Not self-emulsifying | C |

TABLE 5-continued

Exemplary high-concentration pure cannabinoid formulations, according to the present invention.

|  | Function | Formulation A-No terpenes mg | Formulation A-With terpenes mg | Formulation B-No terpenes mg | Formulation B-With terpenes mg |
|---|---|---|---|---|---|
| Largest detected size |  |  | <10μ |  | <10μ |
| Mean particle size |  |  | <2μ |  | <2μ |
| C-T-E |  | 58-0-42 | 48-17-35 | 56-0-44 | 47-16-37 |

Example 5. Disintegration to Fine Particles

Composition F002 of the invention was diluted 1:10 in water. Seconds later, a fine emulsion was formed, with an average particle size of less than 10 microns, as illustrated in FIG. 1.

Example 6. Disintegration to Fine Particles

Figure 2:
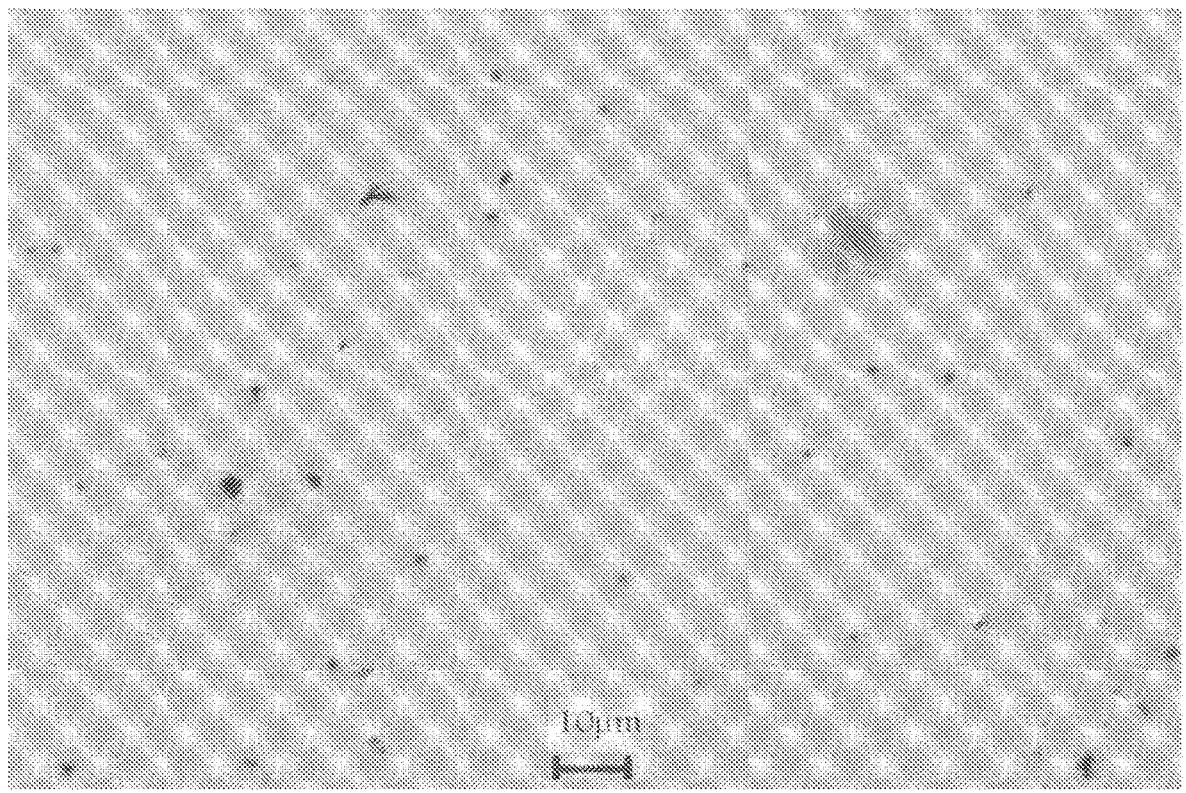
FIG. 2 is a light microscope picture (magnification ×200) of fine particles of formulation F009 post dissolution test of one capsule in USP simulated intestinal fluids.

Composition F009 of the invention was diluted in simulated intestinal fluids (pH 6.4). A fine emulsion was formed, with an average particle size of less than 10 microns, as illustrated in FIG. 2.

Example 7. Disintegration to Fine Particles

Figure 3:
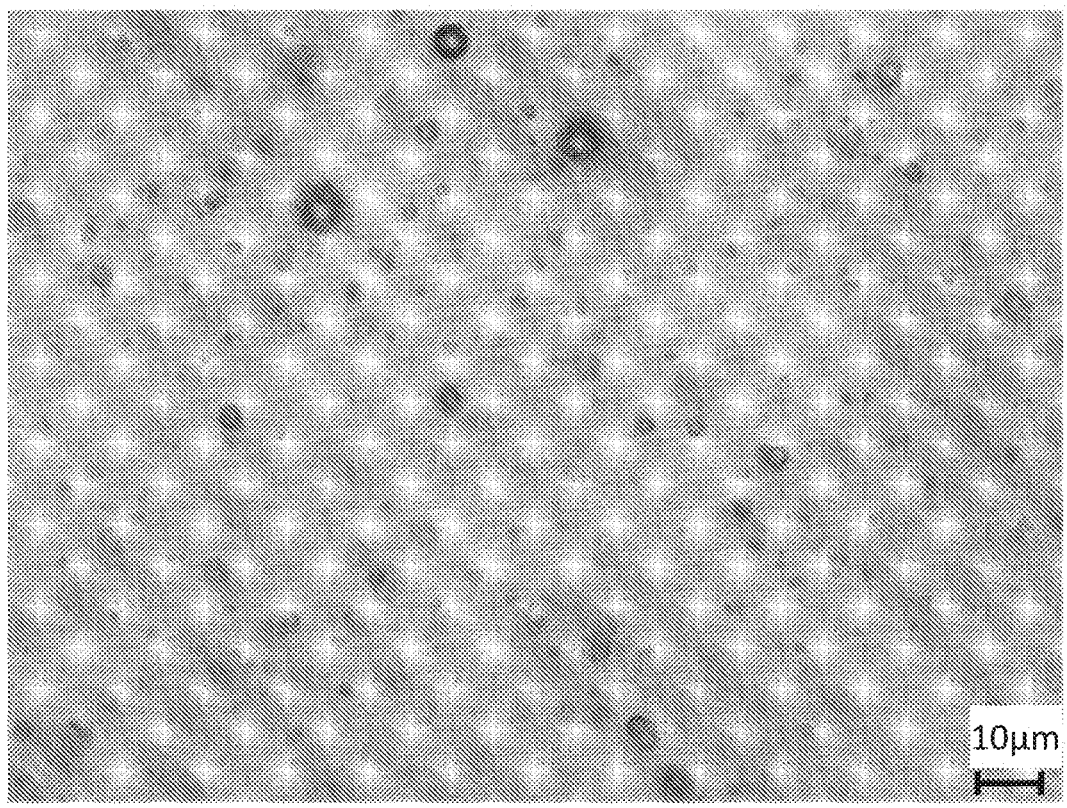
FIG. 3 is a light microscope picture of fine particles of formulation F011 diluted 1:10 in water (magnification ×200).

Composition F011 of the invention was diluted 1:10 in water. A fine dispersion was formed, with an average particle size of less than 10 microns, as illustrated in FIG. 3.

Example 8. Disintegration Profiles

Figure 4:
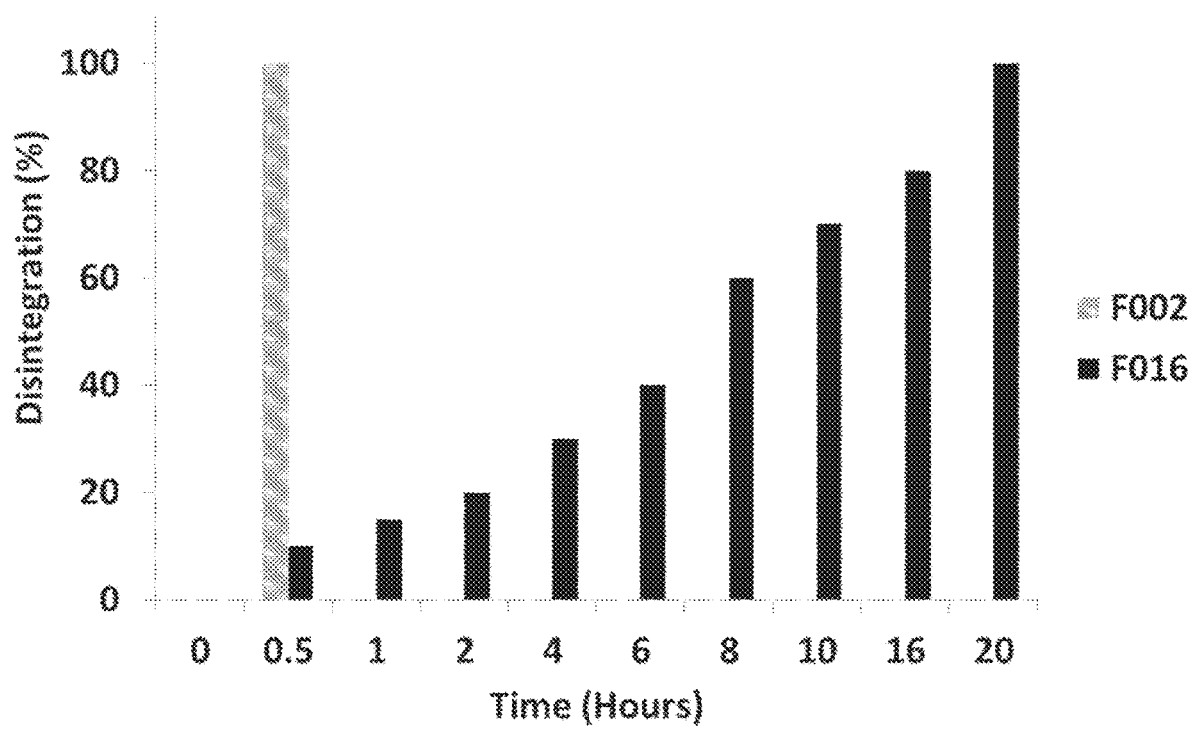
FIG. 4 is a bar graph illustrating the disintegration profile of formulation F002 and F016 in USP simulated intestinal fluids.

Composition F002 of immediate release and Composition F016 with release retarding agents were filled into two parts hard shell capsule and placed in a metal sinker and subjected to USP apparatus type 2 dissolution test with 250 ml simulated intestinal fluids at 37° C.+/−2° C. agitated at 200 RPM. The disintegration of the capsule and the capsule content (FIG. 4) was monitored visually and reported in minutes after start of the test.

Example 9. Disintegration to Fine Particles

Figure 5:
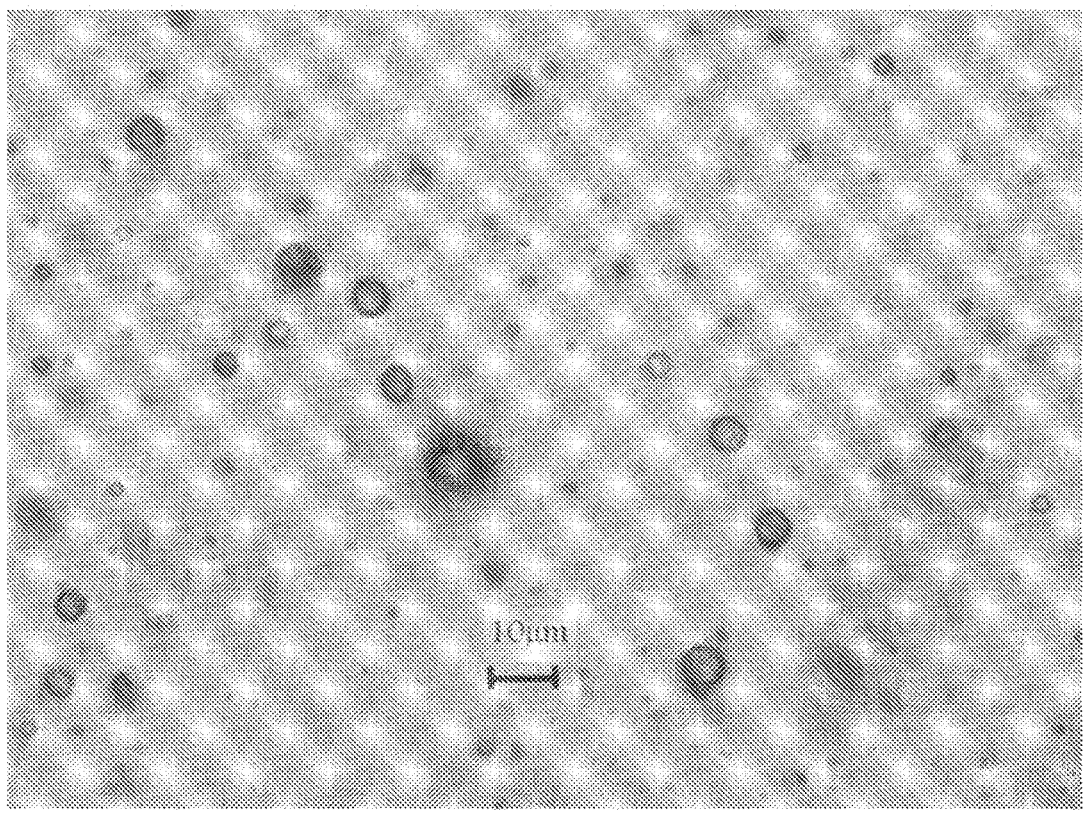
FIG. 5 is a light microscope picture of fine particles of formulation CBD02 formed after dilution 1:10 in water (magnification ×200).
Figure 6:
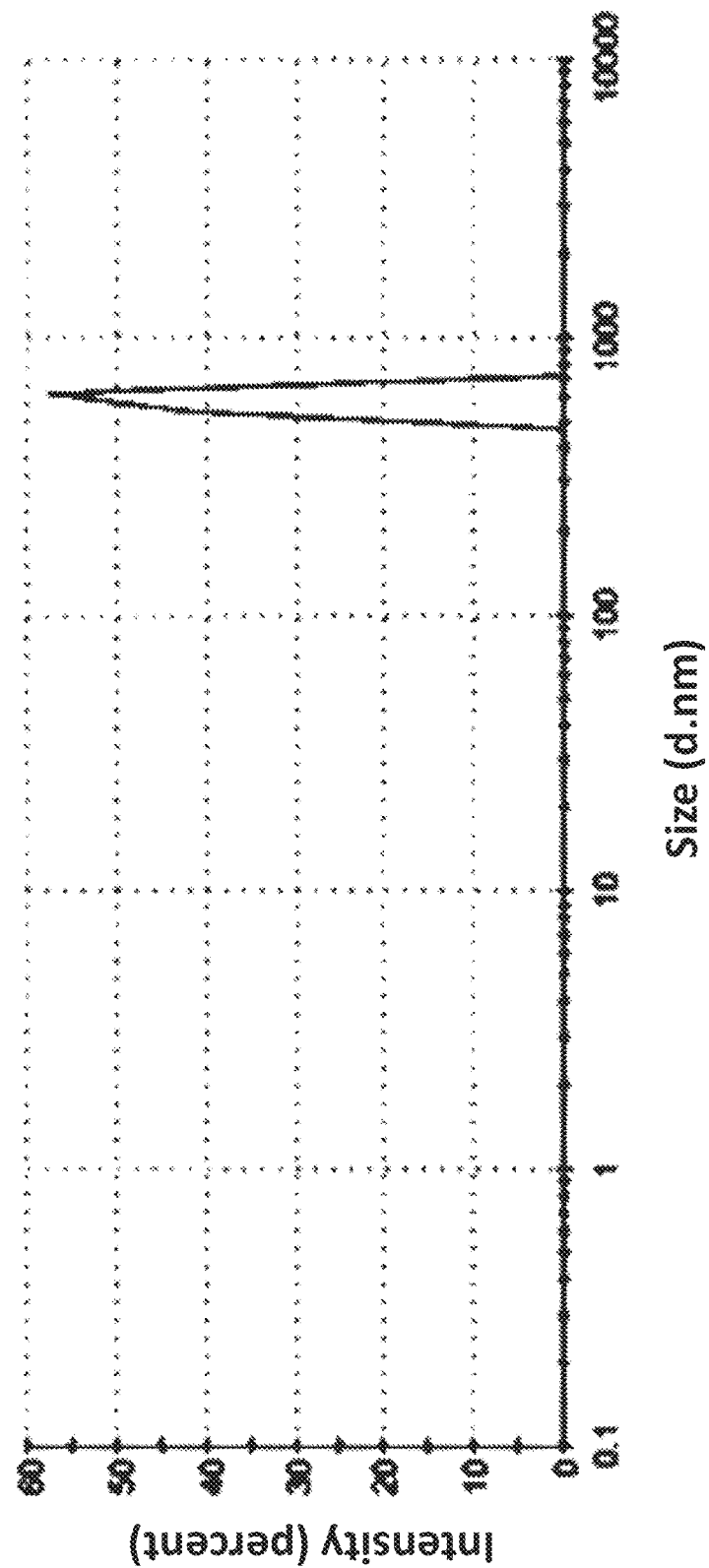
FIG. 6 is a graph illustrating the particle distribution of formulation CBD05.
Figure 7:
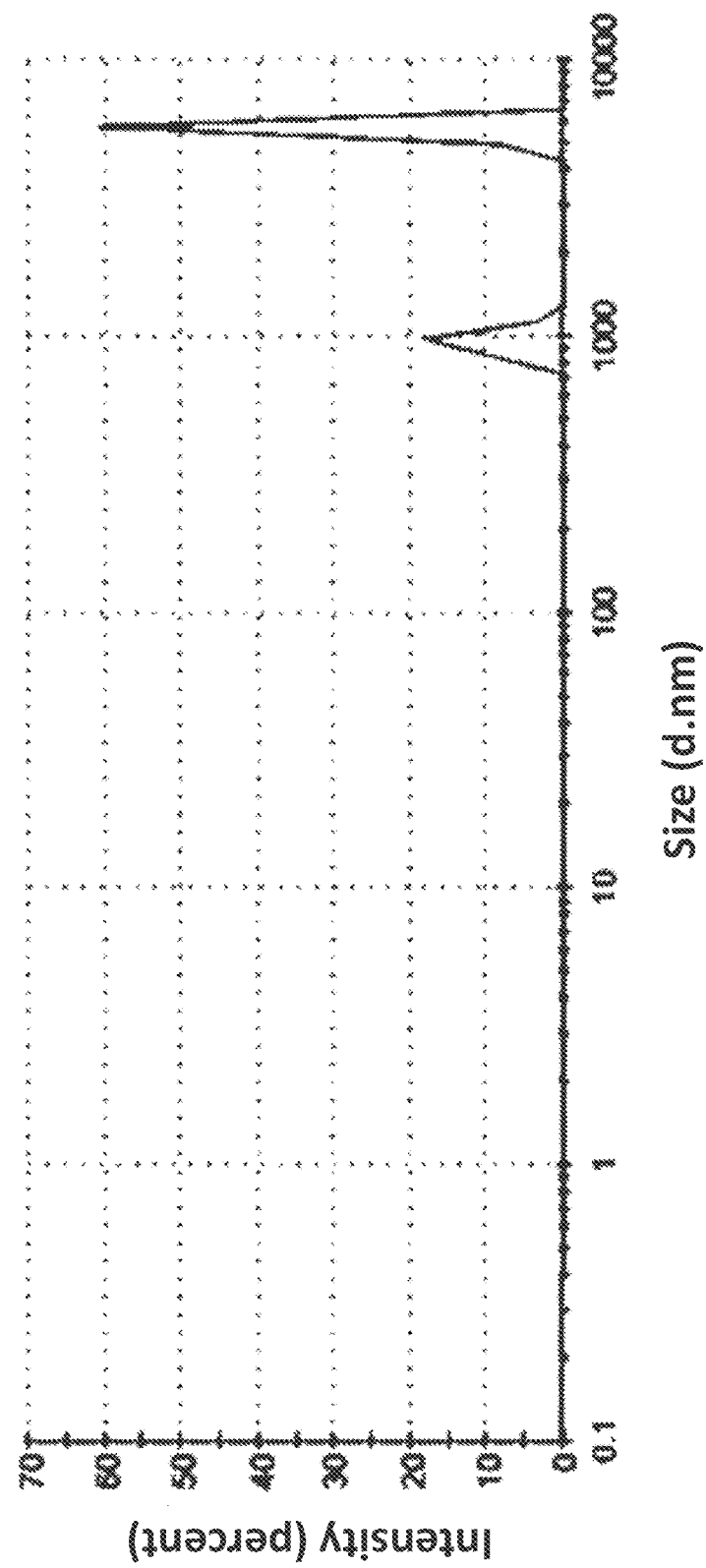
FIG. 7 is a graph illustrating the particle distribution of formulation CBD12.
Figure 8:
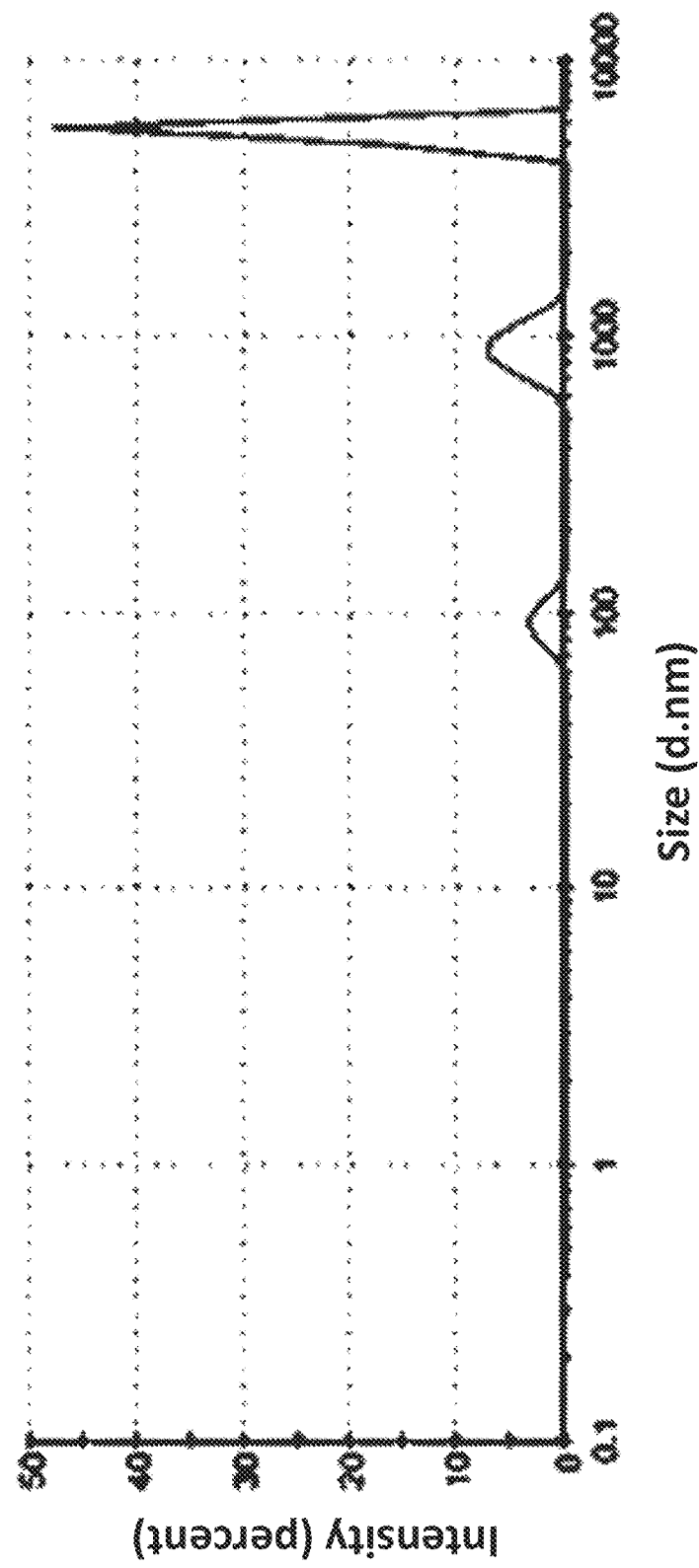
FIG. 8 is a graph illustrating the particle distribution of formulation CBD15.
Figure 9:
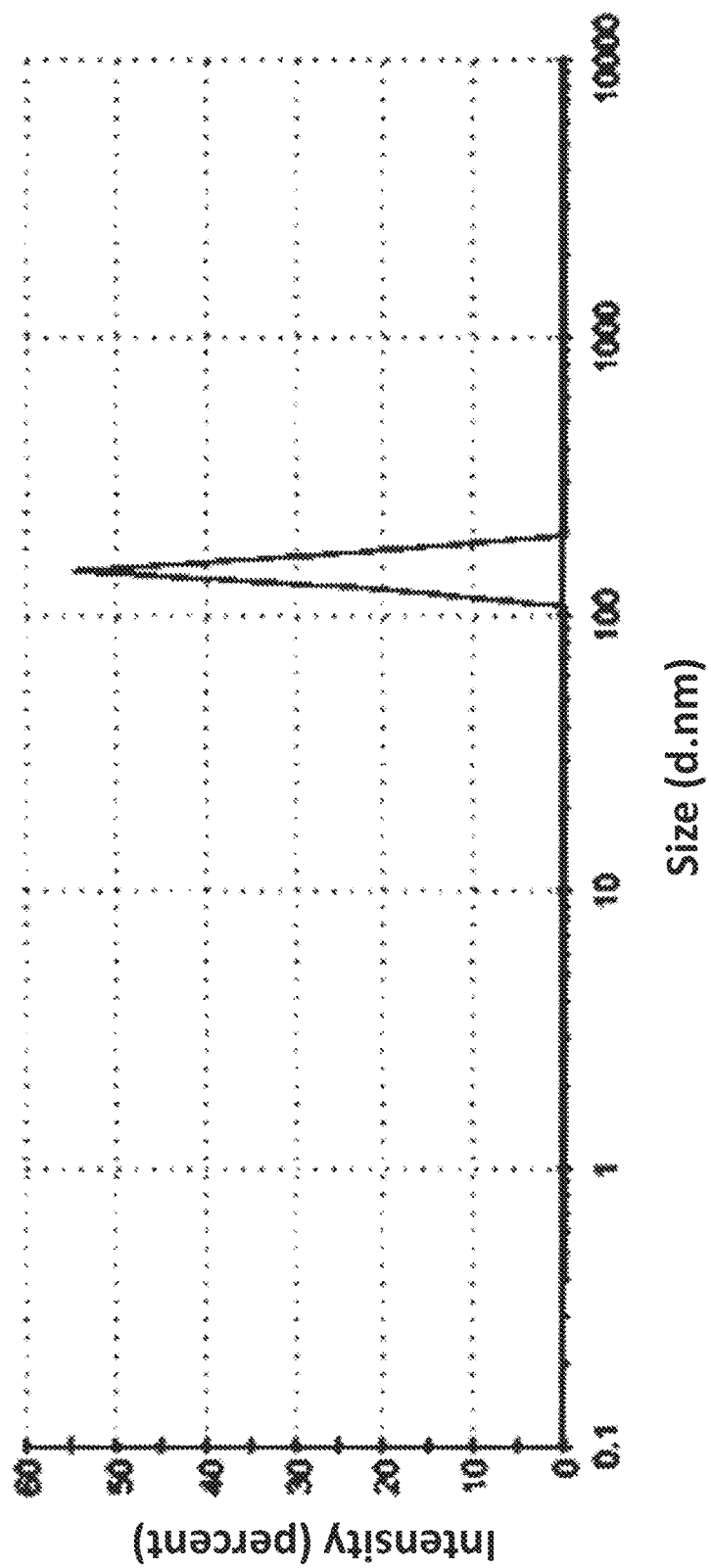
FIG. 9 is a graph illustrating the particle distribution of formulation CBD24.

Composition CBD02 was diluted 1:10 in water. A fine emulsion was formed, with an average particle size of less than 10 microns, as illustrated in FIG. 5.

Example 10. Particle Size Distributions 200 microlitter of Compositions CBD05, CBD12, CBD15 or CBD24 were mixed with 5 ml of purified water and tested with Malvern Zetasizer™ measuring Dynamic light scattering (DLS). Each sample was tested three times and 5 replicates. Particle size distributions are illustrated in FIGS. 6 to 9, respectively. As shown, CBD05 uniformly emulsified to particles of about 579 nm in size, CBD12 emulsified to two species of particles, about 5469 nm (69%) and about 933 nm (31%) in size, CBD15 emulsified to three species of particles, about 5367 nm (64%), about 895 (26%) nm and about 91 nm (10%) in size, and CBD24 uniformly emulsified to particles of about 143 nm in size.

Example 11. Pre-Clinical Studies

TABLE 6

|  | Function | CBD29 mg |
|---|---|---|
| Pure CBD Cannabidiol | Cannabinoid | 48 |
| Pinene | Terpene | 4 |
| Caryophyllene | Terpene | 4 |
| Limonene citronella oil (95% Limonene) | Terpene | 4 |
| TPGS | Emulsifier | 10 |
| Span 80 | Emulsifier | 10 |
| Cremophor EL | Emulsifier | 10 |
| Surphope 1811 | Emulsifier | 10 |
| Total |  | 100 |
| Self-emulsification (score) |  | 3 |
| Grade |  | C |
| Mean particle size |  | <1μ |
| C-T-E |  | 48-12-40 |

Sprague Dawley® Rats, 8 weeks old, weighting 210-230 grams, were dosed for six weeks twice daily with the formulation CBD29 at 600 mg/kg. Of note, 600 mg/kg is 150% of the maximal dose of 400 mg/kg intended for use in human studies. Body weight, blood tests, organ weight and histopathology of liver, heart, lungs, intestines, stomach and other parts of the body did not show any signs of toxicity.

Example 12. Exemplary High-Concentration Pure Cannabidiol Formulations, According to the Present Invention

TABLE 7

|  | Function | CBD30 mg | CBD31 mg | CBD32 mg | CBD33 mg |
|---|---|---|---|---|---|
| Pure CBD Cannabidiol | Cannabinoid | 38 | 38 | 40 | 20 |
| Sesame oil | Triglyceride | 22 | 0 | 0 | 40 |
| Capric/caprulic/triglycerides (Myrtiol 318PH) | Triglyceride | 0 | 20 | 0 | 0 |
| Olive oil | Triglyceride | 0 | 0 | 19 | 0 |

TABLE 7-continued

| | Function | CBD30 mg | CBD31 mg | CBD32 mg | CBD33 mg |
|---|---|---|---|---|---|
| Rosmarinus oil | Terpene | 13.2 | 12.4 | 13 | 14.8 |
| TPGS | Emulsifier | 6.7 | 6.9 | 7 | 6.3 |
| Tween 80 (Polyusobate 80) | Emulsifier | 6.7 | 6.9 | 7 | 6.3 |
| Cremophor EL (Polyoxyl 35 hydrogenated castor oil) | Emulsifier | 6.7 | 6.9 | 7 | 6.3 |
| Surphope 1811 (Sucrose distearate) | Emulsifier | 6.7 | 6.9 | 7 | 6.3 |
| Total | | 100 | 100 | 100 | 100 |
| Self-emulsification (score) | | 3 | 3 | 3 | 3 |
| Grade | | C | C | C | C |
| Mean particle size | | <2µ | <5µ | <5µ | <1µ |
| C - T - E | | 38-13.2-26.8 | 38-12.4-27.6 | 40-13-24 | 20-14.8-25.2 |

Example 13. A Double-Blind Study Evaluating the Safety and Efficacy of a Composition Comprising CBD for the Treatment of BPD Objectives
Primary Objective:

To evaluate preliminary efficacy following treatment of CBD and CBD:THC mixture in a 20:1 ratio (CBD/THC) in adults with BPD. Secondary Objectives: To assess the safety profile of CBD and CBD/THC administration; To evaluate the differences in administration of benzodiazepines and anti-psychotic medication, while treated with CBD and CBD/THC; To evaluate the attenuation influence profile of CBD and CBD/THC 4 weeks after end of administration. Exploratory Objective: To assess population PK of CBD, THC and their metabolites at steady state Endpoints
Efficacy Endpoints
Primary Endpoint:

Proportion of subjects showing improvement (defined as mean change of at least 20%) in Borderline symptoms severity (BSL-23) scale from baseline at week 7 (6 weeks of treatment). Efficacy Secondary Endpoints: Change from baseline to week 7 (6 weeks of treatment) in the following scales: Brief Psychiatric Rating Scale (BPRS), Anxiety: Hamilton Anxiety (HAM-A), Depression: Hamilton Depression (HAM-D), Barratt Impulsiveness Scale (BIS-11), Pittsburgh Sleep Quality Index (PSQI), Columbia-Suicide Severity Rating Scales (C-SSRS), Columbia Non-Suicidal Self-Injury Rating Scale, Sheehan Disability Scale (SDS), Fagerstrom test for nicotine dependence (FTND), Pain Catastrophizing symptoms questionnaire (PCS), Zanarini Rating Scale for BPD (ZAN-BPD), Proportion of subjects who reduced the consumption of approved benzodiazepines and/or anti-psychotic medication in comparison to the baseline.

Safety Endpoints
Safety Outcomes:

Frequency, duration and severity of adverse events (AEs) and serious AEs (SAEs); Clinically significant abnormalities (vital signs, physical examination and safety laboratories).

Tolerability Outcomes:

Proportion of subjects who discontinue the study treatment for any reason; Proportion of subjects who discontinue the study treatment due to AEs PK Endpoints Plasma concentrations of CBD and its metabolites at steady state Overall Study Design and Plan A proof-of-concept, randomized, double-blind, placebo-controlled, fixed-dose titration, investigator-initiated study. The study evaluates the safety, tolerability, efficacy, and population PK at steady state of CBD and CBD/THC in adult patients with BPD. The study intervention is an add-on treatment to existing therapy that the subject has being receiving prior to study start, or receiving concurrent to it. The study includes a Screening period, a Run-in period, a Treatment period, and a Follow-up period.

After signing informed consent and undergoing screening assessments, eligible subjects are randomized on Day 1 in a 1:1:1 ratio to one of three treatment arms: cannabidiol (CBD), cannabidiol and THC (in a ratio of 20:1; CBD/THC) and matching placebo. On Day 1, the subjects enter a one-week Run-in single-blind period and receives placebo. Eligible subjects who successfully completed the Run-in period enter the Treatment period and receive study treatment over 6 weeks according to their assigned randomization group; initially subjects undergo a fixed dose titration over the first two weeks (starting at 200 mg per day to 400 mg/day). Subjects receiving placebo undergo mock titration. After completing the treatment period, subjects enter a 4-week Follow-up period and are monitored for safety and to evaluate the efficacy and attenuation behavior of the study intervention.

An independent Data Safety Monitoring Committee (DSMB) acts in an advisory capacity to the Investigator to monitor subject safety during the study.

Study duration for each participating subject is up to 13 weeks as follows: Screening period: 2 weeks; Run-In: 1 week; Treatment: 6 weeks, Follow up: 4 weeks. The study takes place at 1-4 sites in Israel.

Subject Population
Inclusion Criteria:

Eligible subjects must meet all of the following criteria: Adult subjects, age≥18 years of age, at the Screening visit. Subjects with Diagnostic and Statistical Manual of Mental Disorders (Fifth edition; DSM-5) and Structured Clinical Interview for personality disorders (SCID-PD) diagnosis of borderline personality disorder. Subjects able and willing to comply with the requirements of the protocol at the time of Screening. Women who are of childbearing potential should use an acceptable method for birth control. Subjects able to understand and sign written informed consent to participate in the study.

Exclusion Criteria:

A subject must not meet any of the following criteria: Subjects with bipolar mood disorder. Subjects with schizophrenia. History of unstable angina or acute myocardial infarction within the 12 weeks preceding the screening visit or other clinically significant cardiac disease at the time of screening as judged by the Principal Investigator. Any clinically significant uncontrolled nervous system (clinical evidence of CNS pathology, neurological disorder, head injury, epileptic seizures or convulsions), gastrointestinal (GI), renal, pulmonary, or hepatic concomitant disease that in the Investigator's opinion would preclude patient participation. Evidence of active malignant disease or malignancies diagnosed within the previous one year (except for basal cell carcinoma and uncomplicated—up to stage 1 squamous cell carcinoma that has been excised and cured). Known allergy or hypersensitivity to any of the test compounds or materials. Female patients who are pregnant or lactating or intending to become pregnant during the study. Known history of immunodeficiency (e.g., HIV positive). ALT, AST or ALP>3×ULN or Total Bilirubin >1.5×ULN. Undergone major surgery/surgical therapy for any cause within four weeks prior to enrollment or planned procedure during the study. Any condition that may jeopardize study participation (e.g., clinically significant abnormal screening clinical or laboratory finding during screening), the interpretation of study results or may impede the ability to obtain informed consent (e.g., mental condition). History of illicit drug (other than *cannabis*) or alcohol use disorder (manifested by use of more than 21 units of alcohol per week) within five years. Inability of the participant to be obligated not to use cannabinoids during the study period. Concurrent use or positive urine screening analyses for opiates, cocaine, amphetamines, methamphetamine (previous use of *Cannabis* is not considered to be an exclusion criteria). Use of propoxyphene, buprenorphine, levomethadyl acetate or sodium acetate. Intake of an investigational drug within 30 days prior to baseline. History of mental retardation or documented IQ below 75.

Subject Identification:

A unique enrollment number is assigned when an individual subject is qualified for study enrollment. Before entry, all subjects who signed informed consent are identified by a screening number.

Removal, Replacement, or Early Withdrawal of Subjects from Therapy or Assessment Subjects are free to discontinue their participation in the study at any time and without prejudice to further treatment. The Investigator must withdraw any subject from the study if that subject requests to be withdrawn. Subjects withdrawn from the study are replaced.

Handling of Withdrawals

If a subject is withdrawn from the study or fails to return either at his or her request or at the Investigator's discretion, every effort should be made to determine the reason. This information is recorded on the subject's case report form (CRF). All subjects who withdraw from the study prematurely, regardless of cause, should undergo all early termination assessments. It is vital to obtain follow-up data for any subject withdrawn due to an AE or abnormal laboratory test finding. In any case, every effort must be made to undertake safety follow-up procedures.

Investigational Product

Identity of Investigational Product

Cannabidiol (CBD) is an abundant cannabinoid found in *Cannabis sativa*. It is provided in 100 or 200 mg capsules containing pure CBD (48%) dissolved in a carrier made of mixture of excipients that are terpenes (12%) and emulsifiers (40%). CBD/THC capsules contain CBD and Tetrahydrocannabinol (THC, psychotogenic cannabinoid that is found in the plant), in a ratio of 20:1. It is provided in 100 or 200 mg capsules containing pure CBD:THC (48%) dissolved in a carrier made of mixture of excipients that are terpenes (12%) and emulsifiers (40%). Placebo is a capsule of the same size and constitution of coconut oil and same emulsifiers but without the active ingredients: CBD and THC.

Study Drug Administration

Drug capsules are administered orally twice daily, every morning and before bed-time for 6 weeks. There is a fixed dose titration period: subjects begin treatment with 200 mg/day for the first week and the dose is increased by 100 mg each successive week (end of the 2nd week and the 3rd week), to a maximum of 400 mg/day; subjects continue treatment for another 3 weeks (total of 6 treatment weeks). Subjects receiving placebo undergo mock titration.

Manufacturing

CBD, CBD/THC and Placebo are manufactured by the Manufacturer TEVA-ADIR agricultural cooperation for *cannabis*.

Packaging and Labelling

CBD, CBD/THC and matching Placebo are packaged and labeled by the Manufacturer in accordance with GCP and any other local regulatory requirements.

Storage, Dispensing and Return of the Investigational Product

Study drug is stored at room temperature 15-25° C. (as per manufacturer's labeling). Subjects is requested to return all used and unused capsules to the site at every visit.

Prior and Concomitant Therapy

General Guidelines

All prior treatments received by the subject within 30 days of the initial Screening visit are recorded on the subject's CRF including the treatment's name, indication and the start and stop dates. Any medications (including prescription, over-the-counter, herbal and food supplements and health store products) to be taken during the study are approved by the Investigator. All approved concomitant medications taken by the subject are recorded on the CRF, along with the indication and start and stop dates, dose and dose frequency.

Prohibited Concomitant Medication

The following medications are not permitted during the study: Propoxyphene, Buprenorphine, Levomethadyl acetate, Sodium acetate (all medications are opiates).

Allowed Medications

All concomitant medications to control existing medical condition (anti-psychotic, benzodiazepines, anti-depressants) and/or those taken during the study to treat possible adverse events are allowed, except those which are prohibited. All concomitant medications are recorded in the subject's medical file and on the appropriate CRF page.

Detailed Investigational Plan and Study Procedures

A schedule of events for this study is shown in Table 1.

TABLE 1

A schedule of events.

| Assessment | Screening | Run-In Baseline | | | Treatment Period | | | EOT | Follow-Up period |
|---|---|---|---|---|---|---|---|---|---|
| Visit | 1 | 2 | 3 | 4 | 5 | 6 | 7 | 8 | 9 |
| Study Week | −2 to 0 | 1 | 2 | 3 | 4 | 5 | 6 | 7 | 11 |
| Visit Window | | | | | ±3 days | | | | ±3 days |
| Informed Consent | X | | | | | | | | |
| Medical History/Demographics | X | | | | | | | | |
| Inclusion/Exclusion | X | X | | | | | | | |
| DSM-5 diagnosis of Borderline personality disorder | X | | | | | | | | |
| Complete Physical Examination | X | X | | | | | | | X |
| Vital Signs (blood pressure, heart rate) | X | X | X | X | X | X | X | X | X |
| Electrocardiogram | X | | | | | | | | |
| Population PK Assessments | | | X | | | | | X | |
| Safety Laboratory (hematology, biochemistry, urinalysis) | X | | | | | | | X | |
| Urine Pregnancy Testing | X | | | | | | | X | |
| Serology | X | | | | | | | | |
| Drug of abuse - Urine | X | | | | | | | X | |
| Concomitant Medications | X | X | X | X | X | X | X | X | X |
| Adverse Events | X | X | X | X | X | X | X | X | X |
| Rating scales | | | | | | | | | |
| Borderline symptoms severity (BSL-23) | X | | X | | X | | | X | X |
| Brief Psychiatric Rating Scale (BPRS) | X | | X | | X | | | X | X |
| Hamilton Anxiety (HAM-A) | X | | X | | X | | | X | X |
| Hamilton Depression (HAM-D) | X | | X | | X | | | X | X |
| Barratt Impulsiveness Scale (BIS-11) | X | | X | | X | | | X | X |
| Pittsburgh Sleep Quality Index (PSQI) | X | | X | | X | | | X | X |
| Columbia-Suicide Severity Rating Scales (C-SSRS) | X | | X | | X | | | X | X |
| Columbia Non-Suicidal Self-Injury Rating Scale | X | | X | | X | | | X | X |
| Sheehan Disability Scale (SDS) | X | | X | | X | | | X | X |
| Fagerstrom test for nicotine dependence (FTND) | X | | X | | X | | | X | X |
| Pain Catastrophizing symptoms questionnaire (PCS) | X | | X | | X | | | X | X |
| Zanarini Rating Scale for BPD (ZAN-BPD) | X | | | | | | | X | |
| Dispense Study Drug | | X | X | X | X | X | X | | |
| Collect Study Drug | | | X | X | X | X | X | X | |
| Study Drug accountability | | | X | X | X | X | X | X | |
| Dispense Subject Diary | X | X | X | X | X | X | | | |
| Review Subject Diary/Compliance | | X | X | X | X | X | X | | |

Screening Period (Visit 1/Day −14 to −1):

The purpose and procedures of the study are fully explained to participants. Those wishing to enroll in the study sign a written informed consent prior to initiating any evaluations or procedures.

The following steps and tests are performed at the Screening Visit: Informed consent, Demographic and medical history, Inclusion/Exclusion, Confirmation of diagnosis of BPD according to DSM-5 and Structured Clinical Interview for DSM-5—Personality Disorders (SCID-5—PD), Complete physical examination, Substance abuse history and concomitant medications review, Vital signs, Electrocardiogram (ECG), Safety laboratory (hematology, biochemistry, urinalysis, serology, drug of abuse—urine, urine pregnancy test for female subjects who have childbearing potential), AE recording, Dispense subject diary.

Rating scales: Borderline Symptom List (BSL-23), Brief Psychiatric Rating Scale (BPRS), Hamilton Anxiety (HAM-A), Hamilton Depression (HAM-D), Barratt Impulsiveness Scale (BIS-11), Pittsburgh Sleep Quality Index (PSQI), Columbia-Suicide Severity Rating Scales (C-SSRS), Columbia Non-Suicidal Self-Injury Rating Scale, Sheehan Disability Scale (SDS), Fagerstrom test for nicotine dependence (FTND), Pain Catastrophizing symptoms questionnaire (PCS), Zanarini Rating Scale for BPD (ZAN-BPD).

Run-In/Baseline (Visit 2/Week 1)

Eligible subjects are randomized at Baseline in 1:1:1 ratio to one of three treatment arms: CBD capsules, CBD/THC capsules, placebo capsules. During the Run-in, subjects receive placebo capsules (twice daily) and are evaluated at the end of the Run-in for safety and efficacy.

The following assessments and procedures are performed at the Run-in/Baseline Visit: Assessment of inclusion/exclusion, Abbreviated physical examination, Vital Signs, AE and concomitant medication recording, Dispense study drug, Dispense subject diary, Review subject diary/compliance.

Treatment Period (Visit 3/Week 2 to Visit 8/Week 7)

All subjects who completed the Run-in period, enter a 6-week treatment period and receive their assigned treatment daily (twice per day). Subjects are requested to attend weekly visits at the clinic.

A fixed dose titration is performed; subjects start treatment with 200 mg/day for the first week and the dose is increased by 100 mg each successive week (end of the 2nd week and the 3rd week), to a maximum of 400 mg/day; subjects continue treatment for another 3 weeks (total of 6 treatment weeks). Subjects receiving placebo undergo mock titration.

The following assessment and procedures are done at the weekly Treatment Visits (week 7 is defined as End of Treatment (EOT) visit): Vital signs, AEs and concomitant medication recording, Safety laboratory (hematology, biochemistry, urinalysis, urine drug of abuse, urine pregnancy) on Week 7 only, Assessment of the following rating scales (Weeks 2, 4, and 7/EOT only; the assessment of a given subject is performed by the same assessor): BSL-23; BPRS; HAM-A; HAM-D; BIS-11; C-SSRS; Columbia Non-Suicidal Self-Injury Rating Scale; SDS; FTND; PCS; and ZAN-BPD (on week 7/EOT only), Dispense study drug (excluding Week 7/EOT), Collect study drug, Study drug accountability, Dispense study diary (excluding Week 7/EOT), Review subject diary/compliance, and Blood sampling for population PK the start of week 2 and end of 7 only.
Follow-Up Period (Week 8 to Week 11)
All subjects who completed the study or discontinued prematurely after receiving at least one dose of study intervention, are followed-up for 4 weeks from last dose (EOT visit). These subjects are evaluated on Visit 9/Week 11 for safety and efficacy attenuation behavior of the study intervention. The following study procedures are done on Visit 9/Week 11: Complete physical examination, Vital signs, Serum pregnancy testing, AEs and concomitant medication recording, Administration of the following rating scales: BSL-23; BPRS; HAM-A; HAM-D; BIS-11; C-SSRS; Columbia Non-Suicidal Self-Injury Rating Scale; SDS; FTND; and PCS.
Early Discontinuation Study Visit
If a subject discontinues prematurely from the study, the same procedures planned for EOT visit is conducted.
Efficacy Assessments
Borderline Symptom List (BSL-23)—
BSL-23 is a short version of the full Borderline Symptom List (95 questions, BSL-95, is based on criteria of the DSM-IV) which is a self-rating instrument for specific assessment of borderline-typical symptomatology. In order to reduce patient burden and assessment time, a short version with 23 items (BSL-23) is used.
Brief Psychiatric Rating Scale (BPRS)—
The BPRS consists of a series of 18 items assessing the following psychiatric symptoms: somatic concern, anxiety, emotional withdrawal, conceptual disorganization, guilt feelings, tension, mannerisms and posturing, grandiosity, depressive mood, hostility, suspiciousness, hallucinatory behavior, motor retardation, uncooperativeness, unusual thought content, blunted affect, excitement, and disorientation. The instrument takes approximately 5-10 minutes to complete, following an interview with the patient. The clinician rates each item on a scale ranging from 1 (not present) to 7 (extremely severe). The inventory is geared toward serious psychopathology. While the ratings on individual items are meaningful, the BPRS can yield an overall score, and sets of items can be grouped into categories.
Hamilton Anxiety Scale (HAM-A)—
The HAM-A is aimed at measuring the severity of anxiety symptoms. The scale consists of 14 items, each defined by a series of symptoms, and measures both psychic anxiety (mental agitation and psychological distress) and somatic anxiety (physical complaints related to anxiety). Each item is scored by the clinician on a scale of 0 (not present) to 4 (severe), with a total score range of 0-56, where <17 indicates mild severity, 18-24 mild to moderate severity and 25-30 moderate to severe.
Hamilton Depression (HAM-D)—
HAM-D is a 21-item clinician-administered multiple-choice measure of depression symptom severity. The first 17 of the 21 items contribute to the total score and items 18-21 give additional information not part of the scale, such as paranoia and diurnal variation. Eight items are scored on a 5-point scale, ranging from 0=not present to 4=severe. Nine are scored from 0-2.
Barratt Impulsiveness Scale (BIS-11)—
BIS-11 is a questionnaire designed to assess the personality/behavioral construct of impulsiveness. It is the most widely used instrument for the assessment of impulsiveness. The current version of the BIS-11 is composed of 30 items describing common impulsive or non-impulsive (for reverse scored items) behaviors and preferences. Items are scored on a 4-point scale, ranging from 1=rarely/never to 4=almost always/always).
Pittsburgh Sleep Quality Index (PSQI)—
The PSQI is a self-report questionnaire that assesses sleep quality over the past month (5-10 minutes to complete). It differentiates "poor" from "good" sleep quality by measuring seven areas (components): subjective sleep quality, sleep latency, sleep duration, habitual sleep efficiency, sleep disturbances, use of sleeping medications, and daytime dysfunction over the last month. The sum of scores for these seven components yields one global score between 0 and 21, where lower scores denote a healthier sleep quality.
Columbia-Suicide Severity Rating Scales (C-SSRS)—
The C-SSRS is a questionnaire used for suicide assessment including risk for suicide, severity, and immediacy of that risk, and since 2012 being the standard for measuring suicidal ideation and behavior in clinical trials according to the FDA.
Columbia Non-Suicidal Self-Injury Rating Scale—
Columbia non-suicidal self-injury rating scale is a questionnaire used to predict risk for a future suicidal attempt among high-risk adolescents and emerging adults.
Sheehan Disability Scale (SDS)—
The SDS is a composite of three self-rated items designed to measure the extent to which three major sectors in the patient's life are impaired by panic, anxiety, phobic, or depressive symptoms. This scale uses visual-spatial, numeric, and verbal descriptive anchors simultaneously to assess disability across three domains: work, social life, and family life. The SDS was developed as a treatment outcome measure that would be sensitive to change and to drug placebo differences over time.
Fagerstrom Test for Nicotine Dependence (FTND)—
The FTND is a standard instrument for assessing the intensity of physical addiction to nicotine. The test was designed to provide an ordinal measure of nicotine dependence related to cigarette smoking. It contains six items that evaluate the quantity of cigarette consumption, the compulsion to use, and dependence. In scoring the FTND, yes/no items are scored from 0 to 1 and multiple-choice items are scored from 0 to 3. The items are summed to yield a total score of 0-10. The higher the total Fagerström score, the more intense is the patient's physical dependence on nicotine.
Pain Catastrophizing Symptoms Questionnaire (PCS)—
The PCS instructions ask participants to reflect on past painful experiences, and to indicate the degree to which they experienced each of 13 thoughts or feelings when experiencing pain, on 5-point scales with the end points (0) not at all and (4) all the time. The PCS yields a total score and three subscale scores assessing rumination, magnification and helplessness.
Zanarini Rating Scale for BPD (ZAN-BPD)—
The ZAN-BPD is a brief clinician administered interview to assess severity and change in BPD symptoms. The questions for the measure were adapted from the BPD module of the Diagnostic Interview for DSM-IV Personality Disorders (DIPD-IV) to reflect a 1-week time frame and each of the nine criteria for BPD is rated on a five-point anchored rating scale of 0 to 4, yielding a total score of 0 to 36. Clinical BPD is considered a total Z-scale score of 9 or greater on the scale.

Safety Assessments and Endpoints—

Safety assessments are based on changes from baseline of clinical AEs reported by the subject or observed by the Investigator, concomitant medication use, treatment compliance (e.g., dropouts due to AEs), vital signs, physical examination and laboratory assessments (hematology, blood chemistry).

Adverse Events—

Adverse events are assessed at all study visits throughout the study. Any AEs that occur throughout the study are recorded. Any new AE that occur between scheduled visits are brought to the attention of the Investigator and recorded in the subject's medical file and on the appropriate CRF page.

Concomitant Medication Use—

Use of concomitant medication is recorded at all study visits.

Treatment Compliance—

Study drug accountability is done during treatment period. Study drug are collected every visit and subject diary are reviewed for compliance.

Vital Signs—

Vital signs measurements are recorded at all study visits and include blood pressure, and heart rate after the subject has sat quietly for at least 5 minutes.

Physical Examination—

A complete physical examination is performed according to the schedule of assessments. The physical examination included appearance, eyes, ears, nose, head, throat, neck, chest, lungs, heart, abdomen, extremities, skin, nervous and musculoskeletal system. Weight and height are measured at Screening.

Laboratory Assessments

All routine clinical laboratory assessments are performed by local site laboratory. The laboratory evaluations include: Hematology: Red Blood Cell (RBC) count, hemoglobin (HGB), hematocrit (HCT), Mean Cell Hemoglobin (MCH), Mean Cell Hemoglobin Concentration (MCHC), Mean Corpuscular Volume (MCV), White Blood Cell (WBC) count and differential, platelet count; Serum biochemistry: total protein, albumin, total bilirubin, ALT, AST, GGT, LDH, CPK, alkaline phosphatase, sodium, potassium, calcium, phosphate, BUN, creatinine, total cholesterol, LDL cholesterol, Triglycerides, Lp(a) Lipoprotein; Pregnancy test for women of childbearing potential—serum or urine β-hCG; Urinalysis: pH, glucose, ketones, erythrocytes, leukocytes, protein, drugs of abuse; and Serology: HIV, HBV.

Population PK—

Plasma concentration of CBD, THC and their metabolites, at steady state, are evaluated at start of week 2 before first CBD administration and week 7/EOT.

Statistical Analysis Method

Sample Size Consideration:

Each of the intervention group (CBD and CBD/THC) is considered separately and compared to the placebo group for the purpose of calculation. For the two group comparisons, a sample size of approximately 25 provides a power of 80% to detect a small to medium effect size (equivalent to d=0.7). This is based on repeated measure of response, a moderate within subject correlation of 0.5, and a one-sided significance level of 5%. Therefore, it is concluded that a sample size of 30 participants in each group covers a dropout rate of 10-15%.

Analyzed Population Sets:

Intent-to-Treat (ITT) analysis set includes all patients who are enrolled into the study.

Safety analysis set consists of all randomized patients who received at least one dose of study treatment Efficacy evaluable set consists of patients who have at least one post-baseline efficacy assessment; patients without a post-baseline efficacy assessment is not considered evaluable for the primary efficacy analysis.

PK analysis set includes all enrolled subjects with at least 1 dose of study drug and have PK data Efficacy Analysis Any performed statistical test is a two-sided test (e.g. ANOVA with repeated measures or paired t-test). The required significance level of findings equals to or lower than 5%. Where confidence limits are appropriate, the confidence level is 95%, unless otherwise stated. The relevant tests are conducted to compare primary and secondary endpoints.

Safety Analysis

The safety assessment is based on the frequency of adverse events, on the observation of clinically significant abnormalities of laboratory values, concomitant medication use, vital signs, and physical examination data in the Safety analysis set.

Adverse events: Overall AE as well as AE classified by system organ class and preferred terminology according to the Medical Dictionary for Regulatory Activities (MedDRA) is summarized. Additionally, AE is summarized by severity and relation to study drug. Severe AEs and AEs leading to discontinuation are also being summarized.

Population PK Analysis

The plasma concentrations of CBD, THC and relevant metabolites at steady-state is summarized by sampling time point using descriptive statistics.

The invention claimed is:

1. A capsule consisting essentially of:
   (i) from about 20% to about 90% by weight of a cannabinoid selected from the group consisting of cannabidiol, cannabidiolic acid, tetrahydrocannabinol, tetrahydrocannabinolic acid, cannabigerol, cannabichromene, cannabinol, cannabielsoin, iso-tetrahydrocannabinol, cannabicyclol, cannabicitran, cannabivarin, tetrahydrocannabivarin, cannabidivarin, cannabichromevarin, cannabigerovarin, cannabigerol monomethylether and mixtures thereof;
   (ii) from about 5% to about 50% by weight of a terpene selected from the group consisting of bisabolol, borneol, caryophyllene, carene, camphene, cineol, citronella, eucalyptol, geraniol, guaiol, humulene, isopropyltoluene, isopulegol, linalool, limonene, menthol, myrcene, nerolidol, ocimene, pinene, phytol, pulegone, terpinene, terpinolene, thymol, and mixtures thereof; and
   (iii) from about 5% to about 50% by weight of an emulsifier selected from the group consisting of polysorbate 80, oleoyl polyoxyl-6 glycerides, polyoxyl-35 hydrogenated castor oil, sucrose distearate, tocopherol polyethylene glycol 1000 succinate, lauryl polyoxyl-32 glycerides, sorbitan monooleate, polyglyceryl-3 dioleate, and mixtures thereof,
   wherein the capsule is essentially free of triglycerides and liposomes, and wherein the capsule self-emulsifies in an aqueous medium to produce a plurality of particles having a mean particle size from about 20 microns to about 100 nm.

2. The capsule of claim 1, in which about 10% to about 25% by weight of a viscosity-modifying agent or a mixture of viscosity-modifying agents is present in the capsule.

3. The capsule of claim 1, wherein the weight ratio between the cannabinoid and the terpene is from about 20:1 to about 0.5:1, from about 15:1 to about 1:1, from about 10:1 to about 1:1 or from about 5:1 to about 1:1.

4. The capsule of claim 1, wherein the emulsifier or the mixture of emulsifiers is in an amount from about 5% to about 25% by weight or from about 25% to about 50% by weight of the capsule.

5. The capsule of claim 1, wherein the capsule self-emulsifies in the presence of an aqueous medium to produce a plurality of particles, wherein at least 80% of the particles have a size of 30 microns or less or wherein at least 90% of the particles have a size of 10 microns or less, and wherein the mean particle size by number is below about 2 microns or below about 1 micron.

6. The capsule of claim 1, in which about 1% to about 20% by weight or about 5% to about 15% by weight of at least one release retarding agent or a mixture thereof is present in the capsule for slow release of the cannabinoid or a mixture of cannabinoids upon self-emulsification.

7. The capsule of claim 1, formulated as a hard-shell capsule or as a soft-shell capsule.

8. The capsule of claim 7, wherein there is 150 mg, 200 mg, 300 mg 400 mg, 500 mg 600 mg, 800 mg, 1000 mg or 1200 mg of a cannabinoid or mixture of the cannabinoids per capsule.

9. The capsule of claim 7, wherein the cannabinoid is cannabidiol.

10. The capsule of claim 9, further consisting essentially of a cannabinoid selected from the group consisting of cannabidiolic acid, tetrahydrocannabinol, tetrahydrocannabinolic acid, cannabigerol, cannabichromene, cannabinol, cannabielsoin, iso-tetrahydrocannabinol, cannabicyclol, cannabicitran, cannabivarin, tetrahydrocannabivarin, cannabidivarin, cannabichromevarin, cannabigerovarin, cannabigerol monomethylether and mixtures thereof.

11. The capsule of claim 10, wherein the cannabidiol to cannabinoid of claim 10 weight ratio is about 10:1, or about 15:1 or about 20:1.

* * * * *